United States Patent
Srivastava et al.

(10) Patent No.: US 9,884,885 B2
(45) Date of Patent: Feb. 6, 2018

(54) SYNTHESIS OF LABILE BASE PROTECTED-MODIFIED DEOXY AND MODIFIED RIBO NUCLEOSIDES, CORRESPONDING PHOSPHORAMIDITES AND SUPPORTS AND THEIR USE IN HIGH PURITY OLIGONUCLEOTIDE SYNTHESIS

(75) Inventors: Suresh C. Srivastava, Burlington, MA (US); Naveen P. Srivastava, Burlington, MA (US)

(73) Assignee: CHEMGENES CORPORATION, Wilmington, MA (US)

( * ) Notice: Subject to any disclaimer, the term of this patent is extended or adjusted under 35 U.S.C. 154(b) by 1723 days.

(21) Appl. No.: 13/261,029

(22) PCT Filed: May 19, 2010

(86) PCT No.: PCT/US2010/001494
§ 371 (c)(1),
(2), (4) Date: Nov. 18, 2011

(87) PCT Pub. No.: WO2010/134992
PCT Pub. Date: Nov. 25, 2010

(65) Prior Publication Data
US 2012/0065386 A1    Mar. 15, 2012

Related U.S. Application Data

(60) Provisional application No. 61/216,491, filed on May 18, 2009.

(51) Int. Cl.

| | |
|---|---|
| *C07H 19/04* | (2006.01) |
| *C07H 19/06* | (2006.01) |
| *C07H 19/16* | (2006.01) |
| *C07H 21/02* | (2006.01) |
| *C07H 23/00* | (2006.01) |

(52) U.S. Cl.
CPC ............ *C07H 19/06* (2013.01); *C07H 19/16* (2013.01); *C07H 21/02* (2013.01); *C07H 23/00* (2013.01); *C07H 19/04* (2013.01); *Y02P 20/55* (2015.11)

(58) Field of Classification Search
None
See application file for complete search history.

(56) References Cited

U.S. PATENT DOCUMENTS

| 6,528,639 B2 * | 3/2003 | Usman ................ C07H 19/06 |
| | | 435/91.1 |
| 2006/0142557 A1 * | 6/2006 | Usman ................ C07H 19/04 |
| | | 536/23.1 |

OTHER PUBLICATIONS

Scherr et al. Bioorganic & Medicinal Chemistry Letters (1997), vol. 7, pp. 1791-1796.*
Lackey et al. Nucleic Acids Symposium Series No. 52 (2008), pp. 35-36.*
Ashley JACS (1992), vol. 114, pp. 9731-9736.*
Ohkubu et al. Nucleic Acids Research (2008), vol. 2008, pp. 1952-1964.*
Brown et al. J. Chem. Soc., Chem. Commun. (1989), pp. 891-893.*
Donga et al. Can. J. Chem. (2007), vol. 85, pp. 274-282.*

* cited by examiner

*Primary Examiner* — Patrick T Lewis
(74) *Attorney, Agent, or Firm* — Law Offices of Indu M. Anand

(57) ABSTRACT

This invention relates to novel method of synthesis of RNA utilizing N-2-acetyl protected guanine as nucleoside base, nucleosides, succinates, phosphoramidites, corresponding solid supports that are suitable for oligo deoxy nucleosides and RNA oligonucleotide synthesis. Our discovery using N-acetyl protected guanine as nucleoside base protecting group, which is significantly faster base labile protecting group, yet significantly more stable than commonly utilized-2-isobutyryl guanosine is a novel approach to obtain highest purity oligonucleotides. This approach is designed to lead to very high purity and very clean oligonucleotide, after efficient removal of the protecting groups, including acetyl group from guanine and to produce high purity therapeutic grade DNA oligonucleotides, RNA oligonucleotides, diagnostic DNA, diagnostic RNA for microarray platform. The deprotection of acetyl protecting groups of the natural deoxy and ribonucleosides occurs under substantially reduced time in contact with mild deprotection conditions such as mild bases, secondary amines for removal of such groups under such conditions would allows synthesis of various DNA and RNA of highest purity for diagnostics and therapeutic application. This approach is designed to lead to high purity large scale therapeutic grade oligonucleotide chimeras which consist of fluoro sugar modification in conjunction with deoxy nucleosides, ribonucleosides, modified base and modified sugar nucleosides. This approach is further designed to use acetyl guanine protecting group when other bases are sensitive nucleoside, and for use in oligo peptide synthesis and for support bound oligo nucleotides.

5 Claims, 17 Drawing Sheets

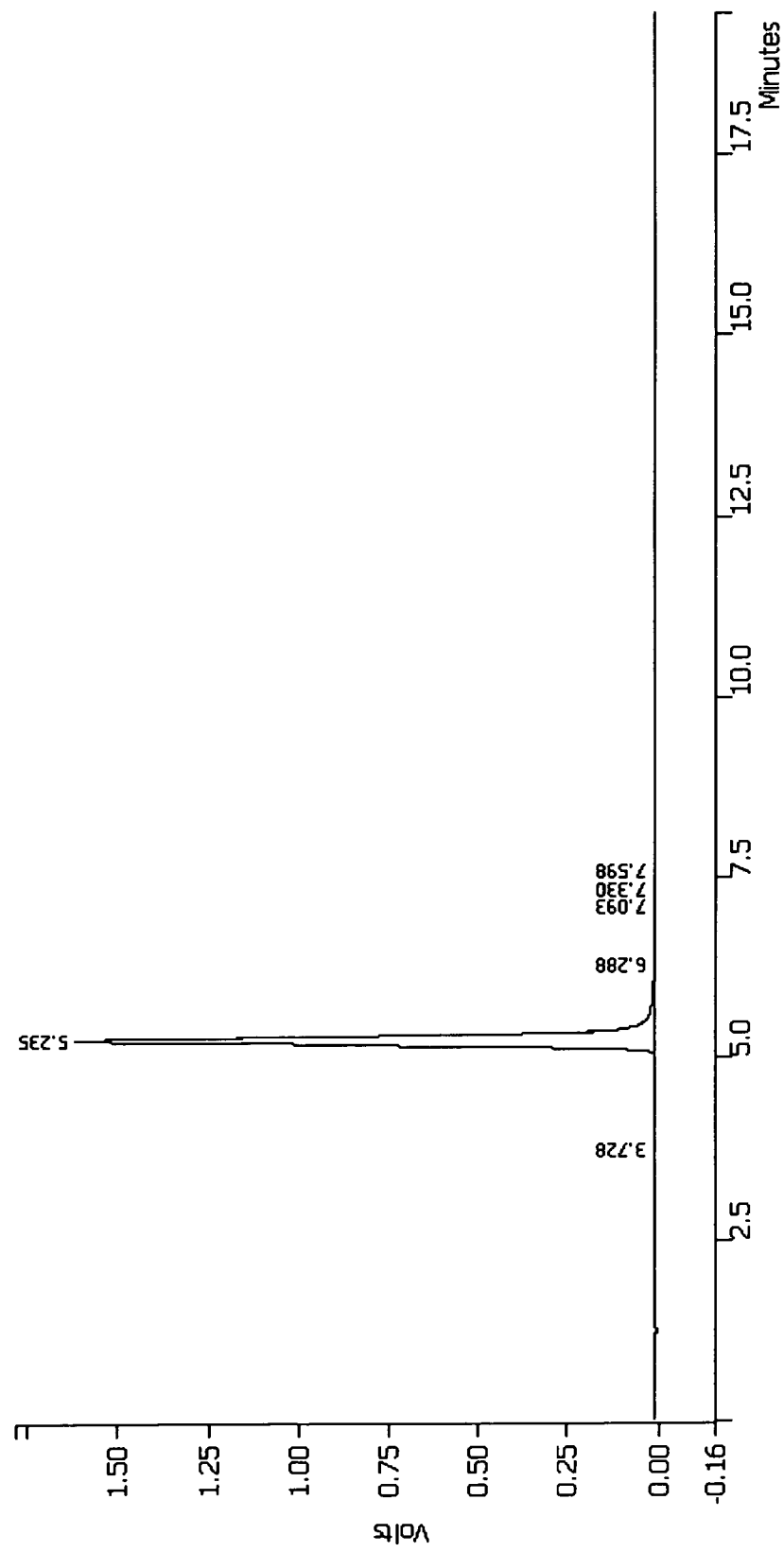
Fig.1a: HPLC Chromatogram of 5'-DMT –ribo Guanosine (n-acetyl)

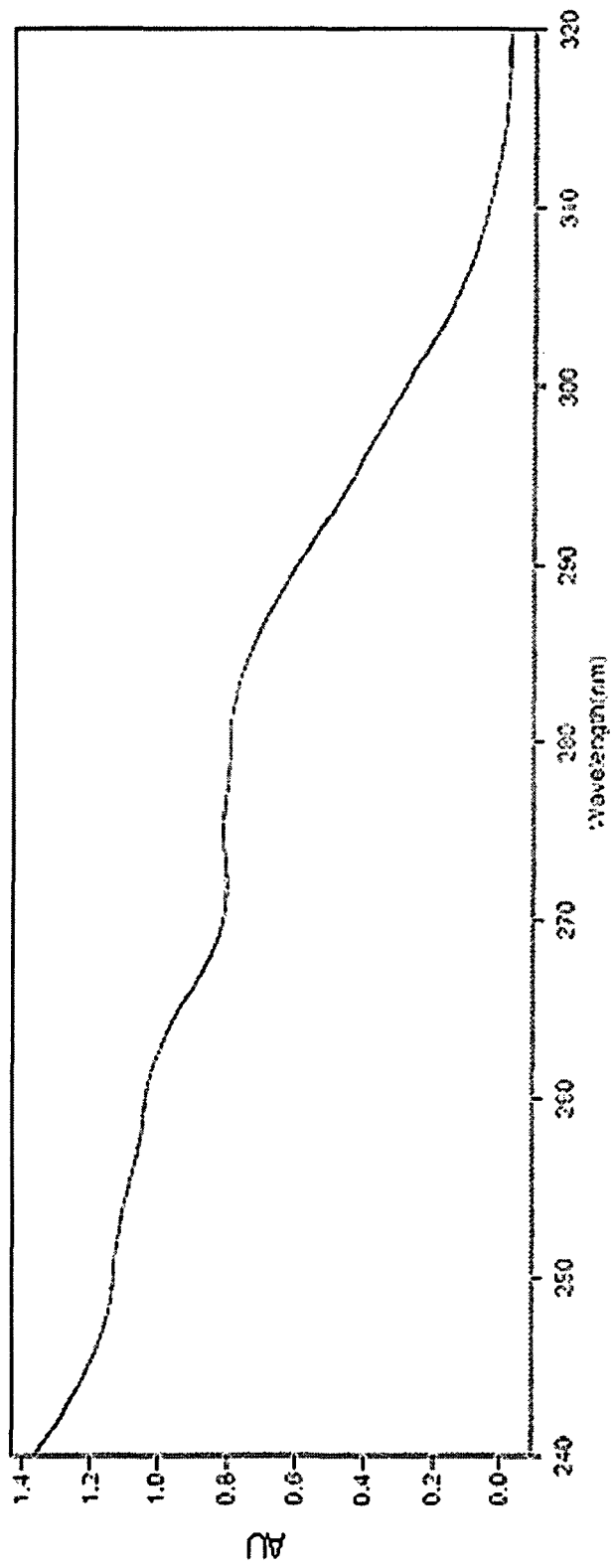
Fig.1b: UV Analysis of 5'-DMT–ribo Guanosine (n-acetyl)
| | A | B | C | D | E | F | G | H |
|---|---|---|---|---|---|---|---|---|
| 1 | 105361.000 | | 1 | 2 | 3 | 5 | 6 | Emax |
| 2 | Cycle01 | nm | 250.0 | 260.0 | 280.0 | 250/260 | 260/280 | 250.0 |
| 3 | Manual | A | 1.133 | 1.042 | 0.794 | 1.087 | 1.312 | 17667 |
Fig.1c: Table of the UV Analysis of 5'-DMT–ribo Guanosine (n-acetyl)

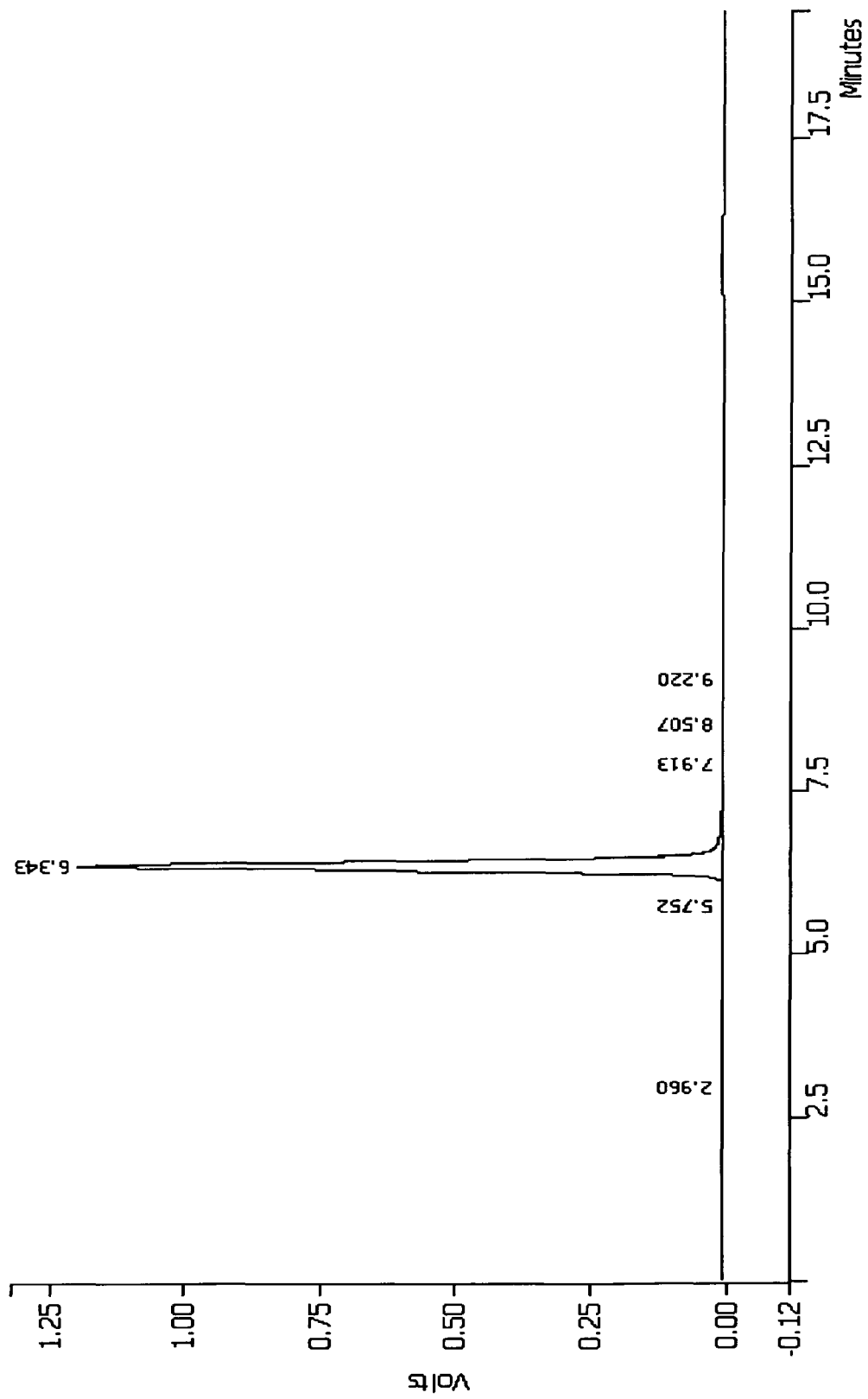
Fig.2a: HPLC Chromatogram of 5'-DMT-2'-TBDMS-ribo Guanosine (n-acetyl)

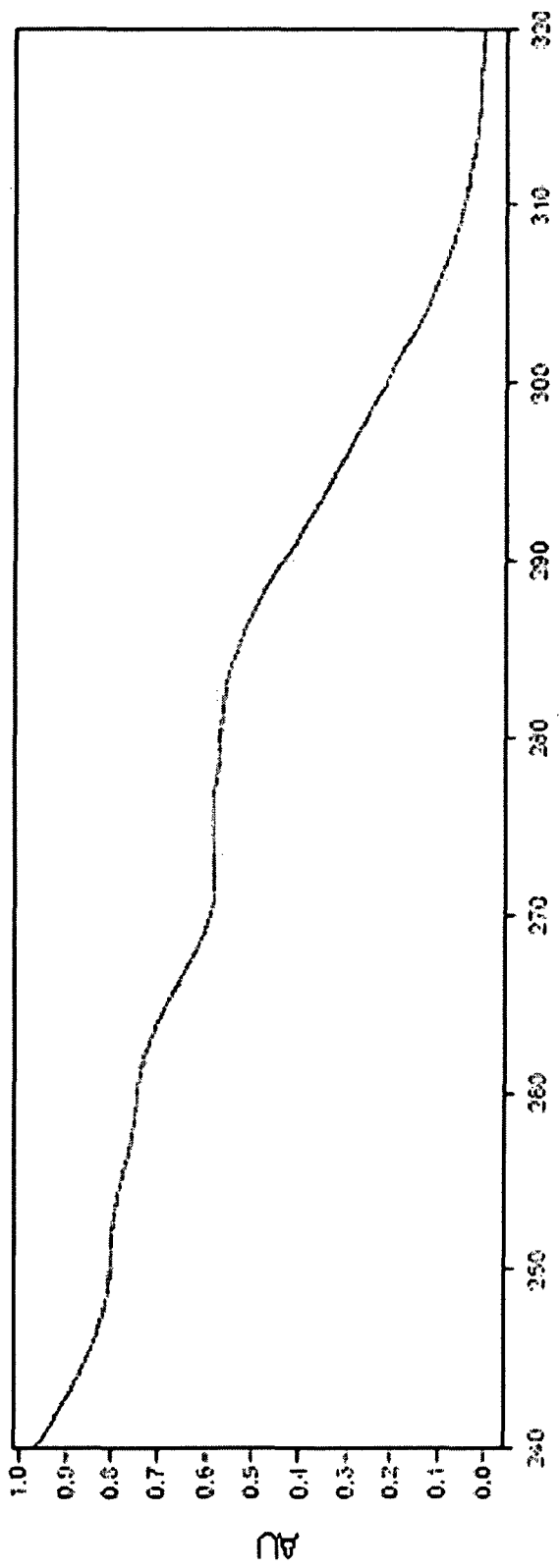
Fig.2b: UV Analysis of 5'-DMT –2'-TBDMS-ribo Guanosine (n-acetyl)
| | A | B | C | D | E | F | G | H |
|---|---|---|---|---|---|---|---|---|
| 1 | PS105-17 | | 1 | 2 | 3 | 4.0 | 5.0 | Emax |
| 2 | Cycle01 | nm | 250.0 | 260.0 | 280.0 | 250/260 | 260/280 | 250.0 |
| 3 | Manual | A | 0.803 | 0.745 | 0.569 | 1.078 | 1.310 | 22695 |
| 4 | Cycle02 | nm | 250.0 | 260.0 | 280.0 | | | |
| 5 | Manual | A | 0.803 | 0.745 | 0.569 | 1.077 | 1.309 | 22695 |
| 6 | Cycle03 | nm | 250.0 | 260.0 | 280.0 | | | |
| 7 | Manual | A | 0.803 | 0.745 | 0.569 | 1.078 | 1.310 | 22695 |
| 8 | Ave. Value | | | | | 1.078 | 1.310 | 22695 |
Fig.2c: Table of the UV Analysis of 5'-DMT –2'-TBDMS-ribo Guanosine (n-acetyl)

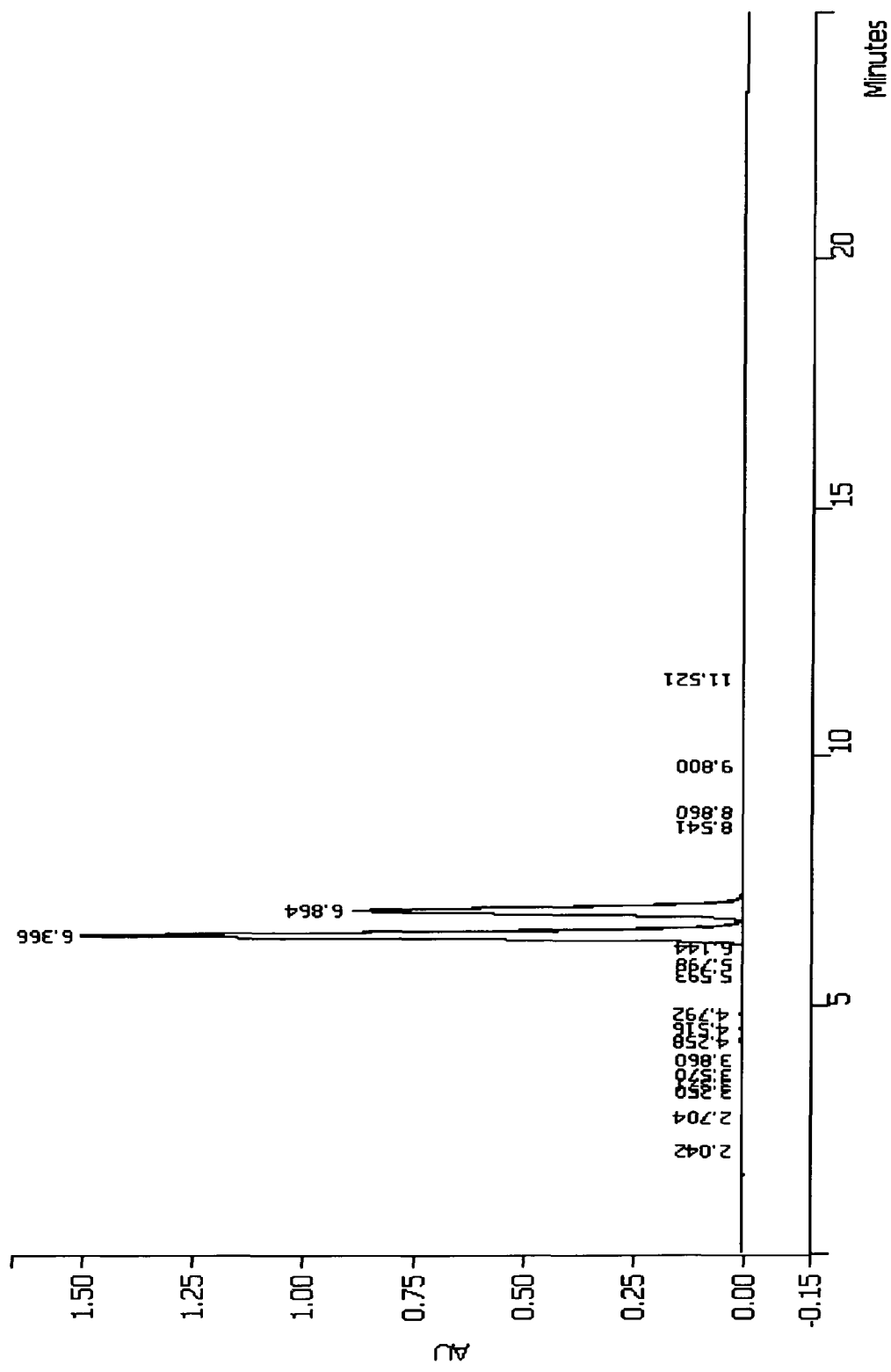
Fig.3a: HPLC Chromatogram of 5'-DMT-2'-TBDMS-ribo Guanosine (n-acetyl)-phosphoramidite

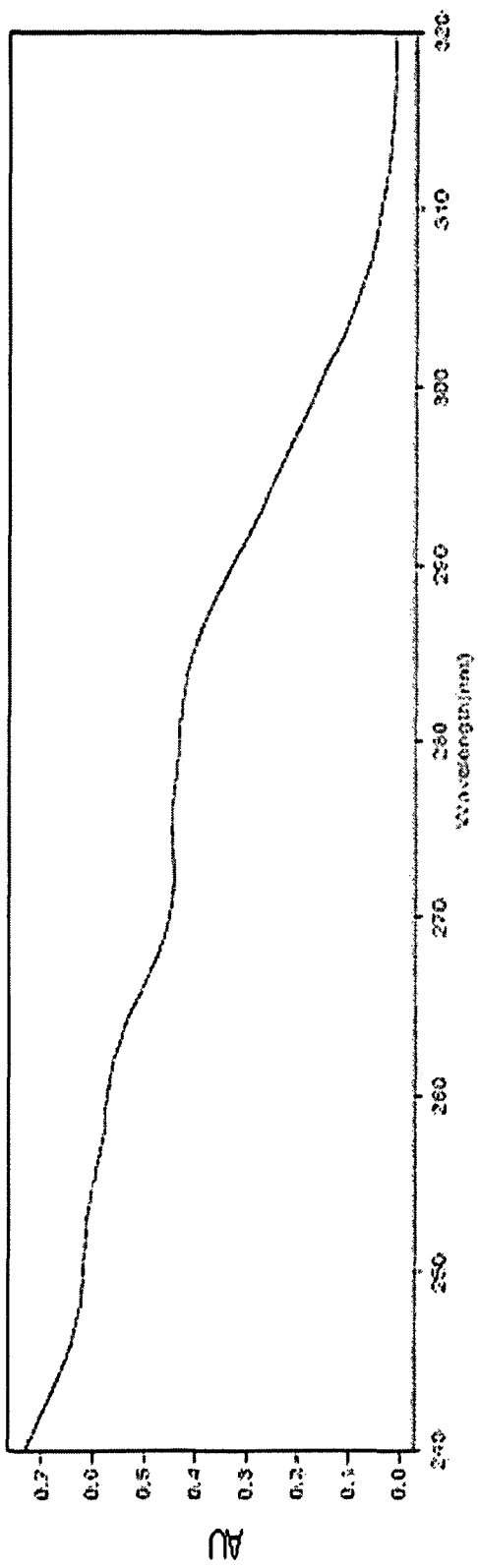
Fig.3b: UV Analysis of 5'-DMT –2'-TBDMS-ribo Guanosine (n-acetyl)-phosphoramidite
| | A | B | C | D | E | F | G | H |
|---|---|---|---|---|---|---|---|---|
| 1 | KP114-14 | | | | | | | |
| 2 | | nm | 1 | 2 | 3 | 4.0 | 5.0 | Emax |
| 3 | Cycle01 | | 250.0 | 260.0 | 280.0 | 250/260 | 260/280 | 250.0 |
| 4 | Manual | A | 0.620 | 0.574 | 0.435 | 1.081 | 1.319 | 20142 |
| 5 | Cycle02 | nm | 250.0 | 260.0 | 280.0 | | | |
| | Manual | A | 0.620 | 0.573 | 0.434 | 1.081 | 1.320 | 20142 |
Fig.3c: Table of the UV Analysis of 5'-DMT –2'-TBDMS-ribo Guanosine (n-acetyl)-phosphoramidite

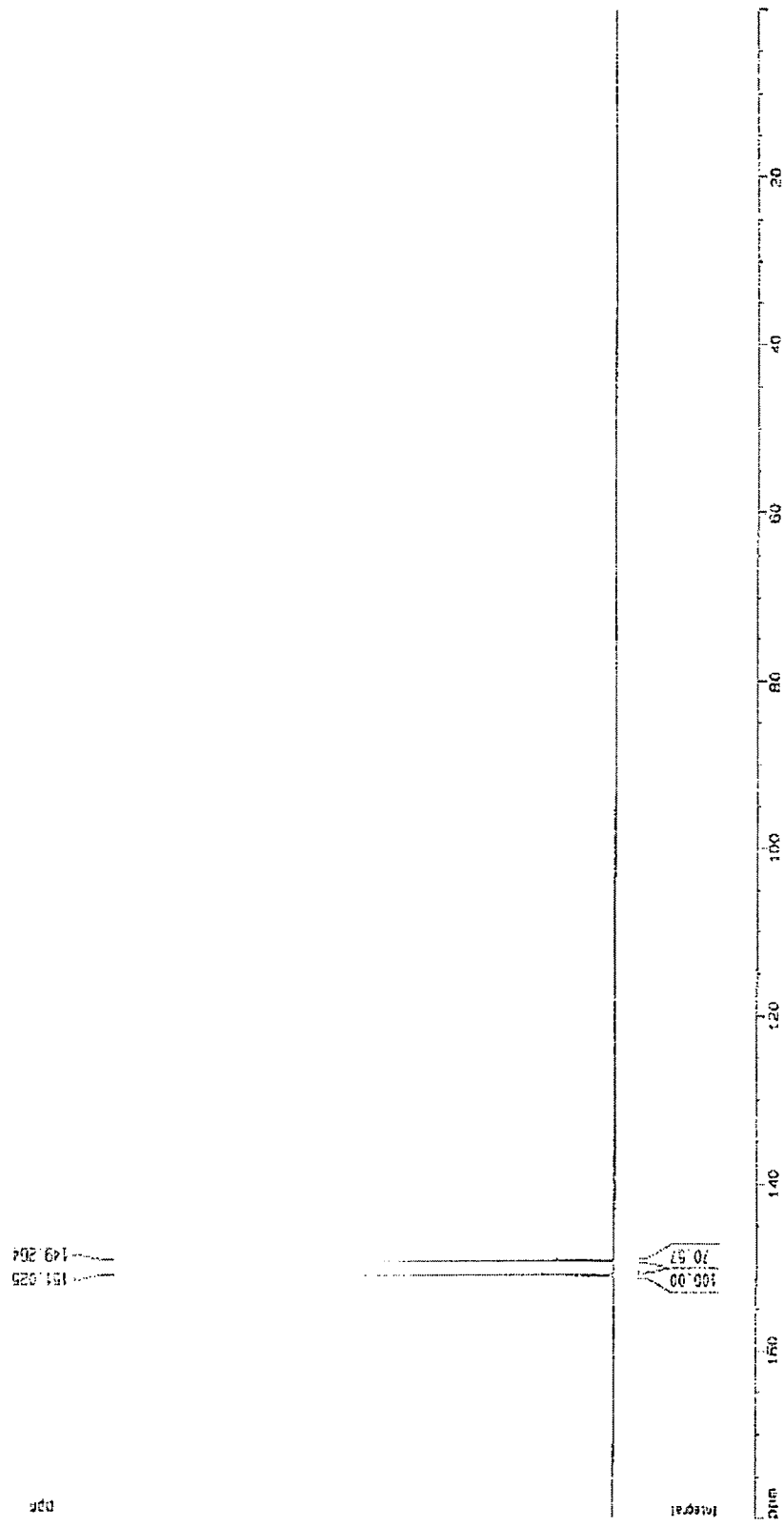
Fig.3d: 31P NMR Spectrum of 5'-DMT –2'- TBDMS -ribo Guanosine (n-acetyl)-phosphoramidite

Example of RNA synthesis #1:
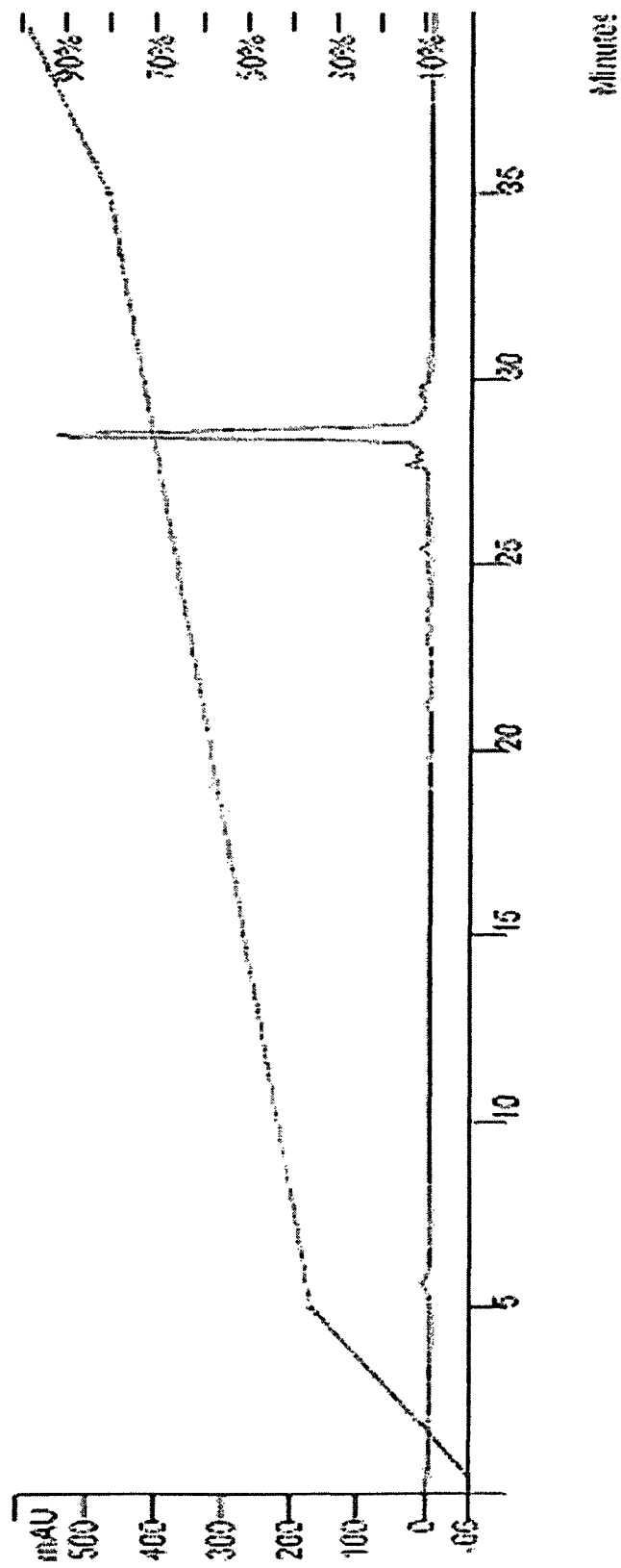
Fig.4a: HPLC Chromatogram of purified RNA Sequence (G7799G97GAAAGA79GA9A9AGAGG7).
Lot No. CH5-9R-45-01
After purification purity: 91.3%
Note:1. N-2-acetyl-ribo-Guanosine-2'-TBDMS-3'-CNET Phosphoramidite was utilized in the chimera RNA Synthesis.
2. The sequence contains 2'-Fluoro C and 2'-Fluoro-U.
7 denotes 2'-Fluoro C base and #9 denote 2'-Fluoro U base.

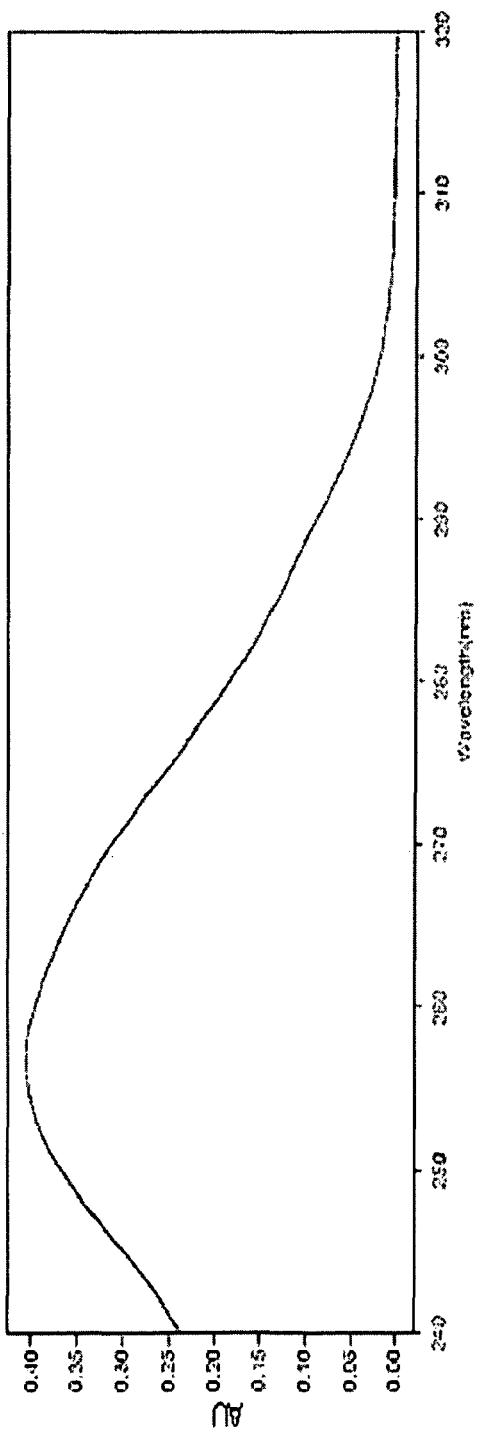

Fig.4b: UV Analysis of purified RNA Sequence (G7799G97GAAAGA79GA9A9AGAGG7).
Lot No. CH5-9R-45-01
Note: 1. N-2-acetyl-ribo-Guanosine-2'-TBDMS-3'-CNET Phosphoramidite was utilized in the chimera RNA Synthesis.
2. The sequence contains 2'-Fluoro C and 2'-Fluoro-U.
7 denotes 2'-Fluoro C base and #9 denote 2'-Fluoro U base.

Batch : 041109-E.sre

| | A | B | C | D | E | F | G |
|---|---|---|---|---|---|---|---|
| 1 | 041109-E | | 1 | 2 | 3 | 5 | 6 |
| 2 | Cycle01 | nm | 250.0 | 260.0 | 280.0 | 250/260 | 260/280 |
| 3 | Manual | A | 0.367 | 0.397 | 0.185 | 0.925 | 2.140 |

Fig.4c: Table of UV Analysis of purified RNA Sequence (G7799G97GAAAGA79GA9A9AGAGG7).
Lot No. CH5-9R-45-01
Note: 1. N-2-acetyl-ribo-Guanosine-2'-TBDMS-3'-CNET Phosphoramidite was utilized in the chimera RNA Synthesis.
2. The sequence contains 2'-Fluoro C and 2'-Fluoro-U.
7 denotes 2'-Fluoro C base and #9 denote 2'-Fluoro U base.

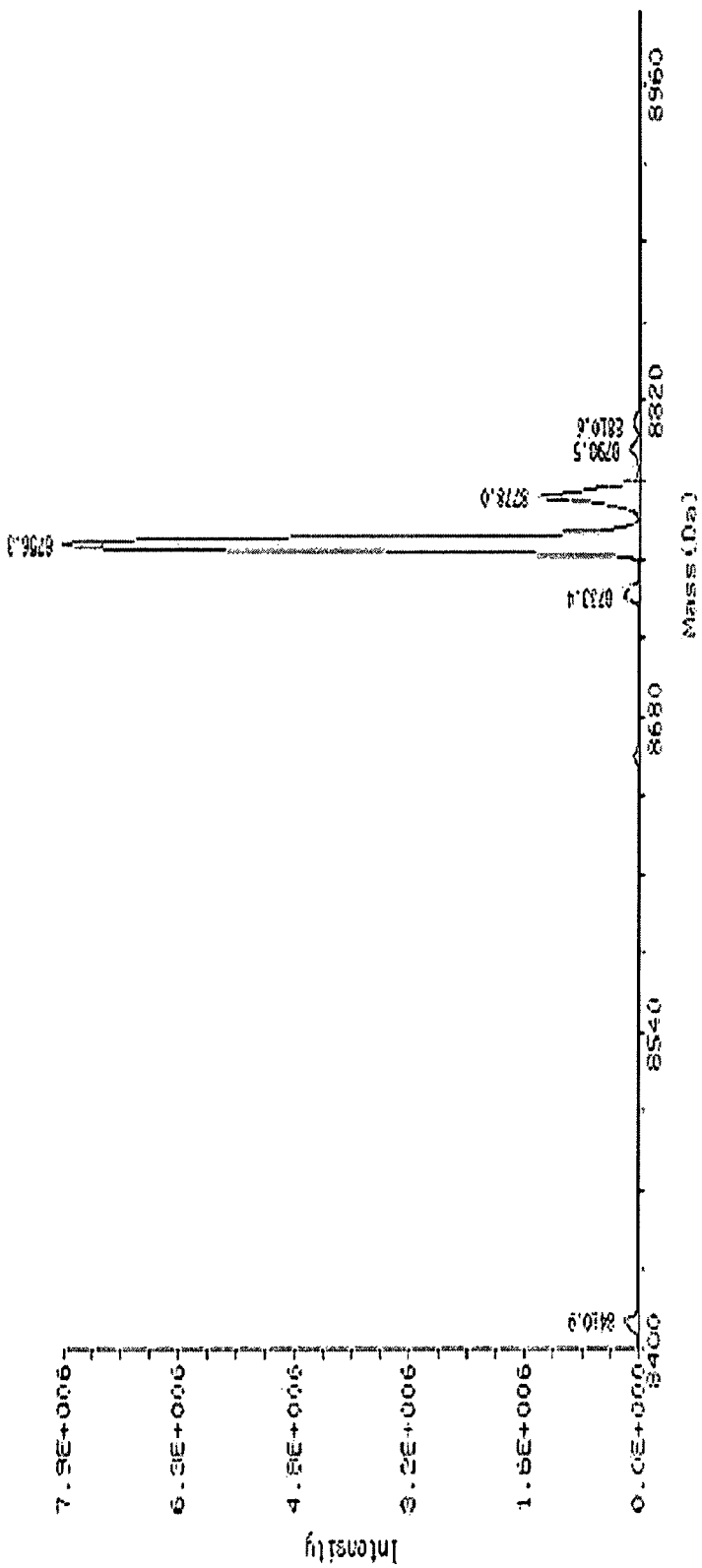
Fig.4d: ESI-MS Analysis of purified RNA Sequence (G7799G97GAAAGA79GA9A9AGAGG7).
Lot No. CH5-9R-45-01
Targeted mass: 8757.5
Observed Mass: 8756.3
Note:1. N-2-acetyl-ribo-Guanosine-2'-TBDMS-3'-CNET Phosphoramidite was utilized in the chimera RNA Synthesis.
2. The sequence contains 2'-Fluoro C and 2'-Fluoro-U.
7 denotes 2'-Fluoro C base and #9 denote 2'-Fluoro U base.

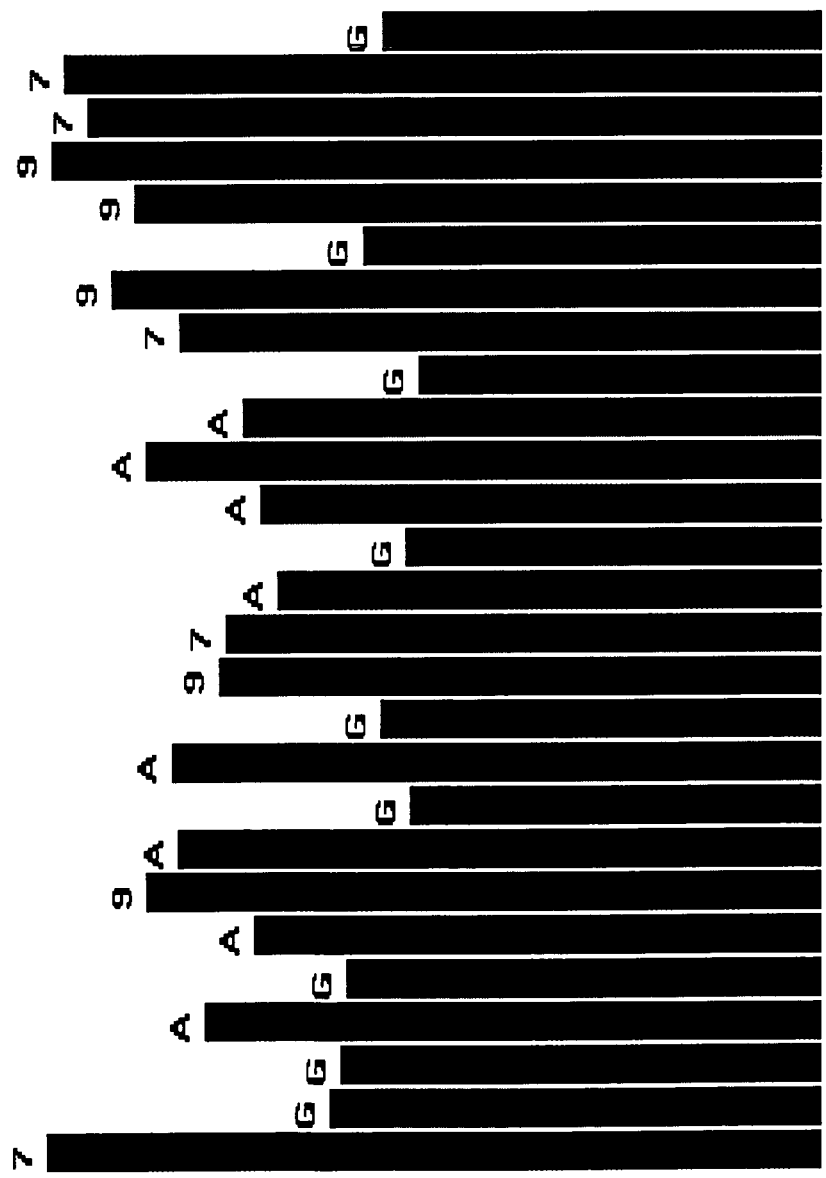
Fig. 4e: Synthesis Report of RNA Sequence (G7799G97GAAAGA79GA9A9AGAGG7).
Lot No. CH5-9R-45-01
Note: 1. N-2-acetyl-ribo-Guanosine-2'-TBDMS-3'-CNET Phosphoramidite was utilized in the chimera RNA Synthesis.
2. The sequence contains 2'-Fluoro C and 2'-Fluoro-U.
7 denotes 2'-Fluoro C base and #9 denote 2'-Fluoro U base.

Example of RNA synthesis #2:
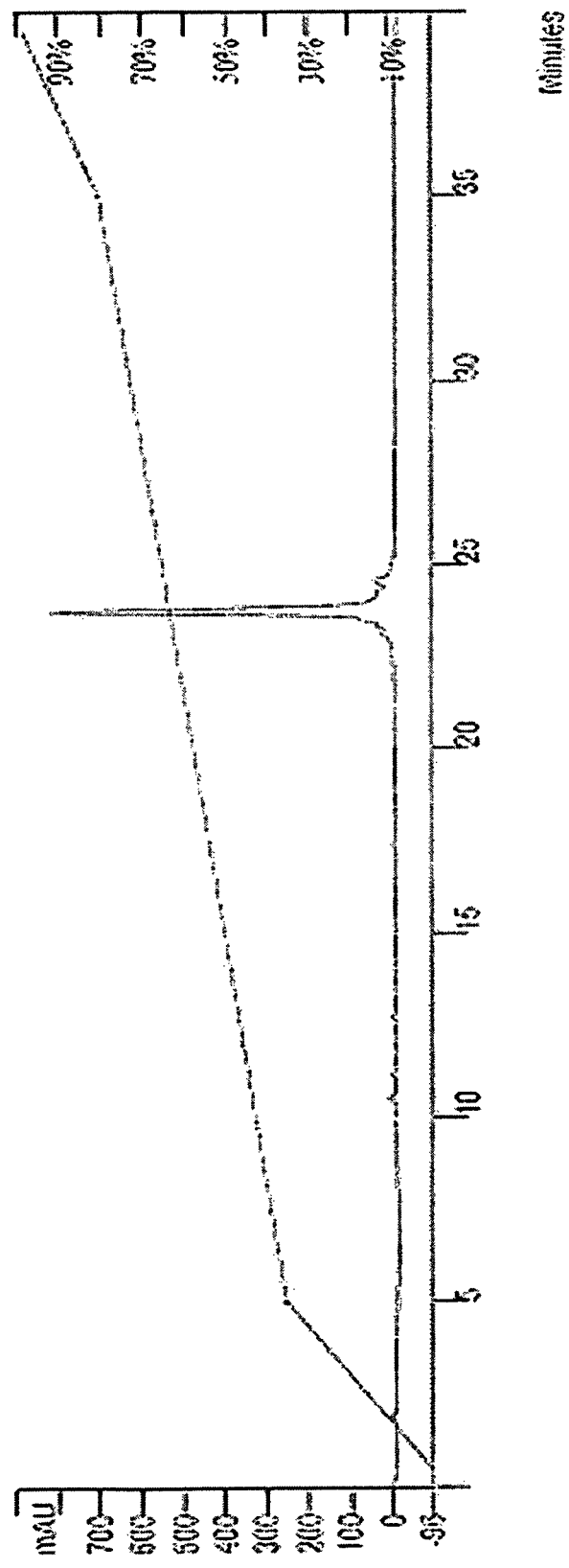
Fig.5a: HPLC Chromatogram of purified RNA Sequence (7979A777A77A9AAA99A7G99G9A9GG9G7A7G9AGAG).
Lot No. CH5-10R-31-01
After purification purity: 90.53%
Note: 1. N-2-acetyl-ribo-Guanosine-2'-TBDMS-3'-CNET Phosphoramidite was utilized in the chimera RNA Synthesis.
2. The sequence contains 2'-Fluoro C and 2'-Fluoro-U.
7 denotes 2'-Fluoro C base and #9 denote 2'-Fluoro U base.

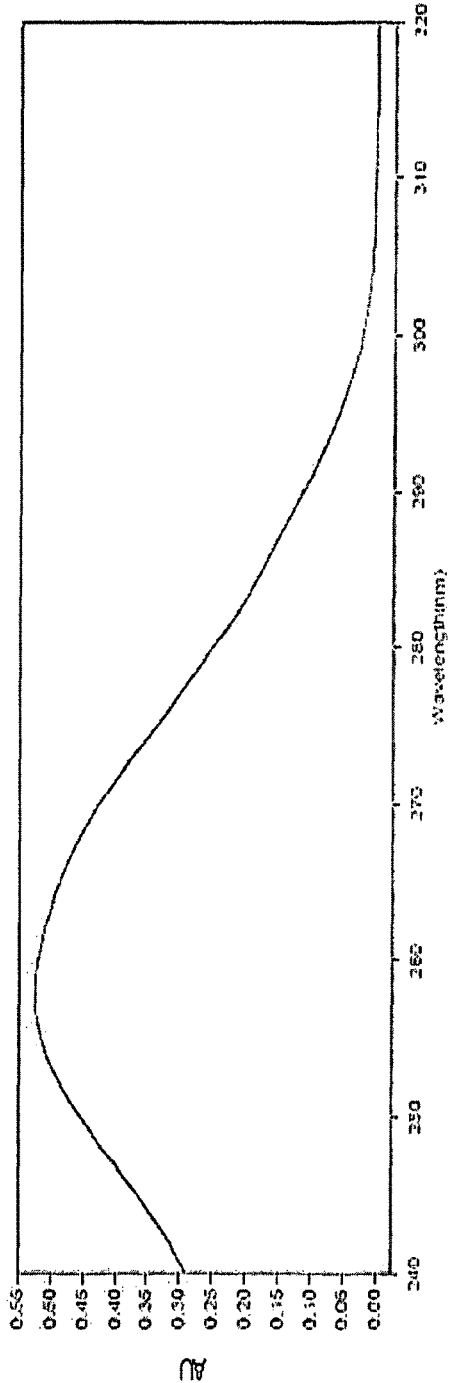

Fig.5b: UV Analysis of purified RNA Sequence (7979A777A77A9AAA99A7G99G9A9GG9G7A7G9AGAG).
Lot No. CH5-10R-31-01
Note: 1. N-2-acetyl-ribo-Guanosine-2'-TBDMS-3'-CNET Phosphoramidite was utilized in the chimera RNA Synthesis.
2. The sequence contains 2'-Fluoro C and 2'-Fluoro-U.
7 denotes 2'-Fluoro C base and #9 denote 2'-Fluoro U base.

Batch : 041109-K.sre

| | A | B | C | D | E | F | G |
|---|---|---|---|---|---|---|---|
| 1 | 041109-K | | | | | | |
| 2 | Cycle01 | nm | 250.0 | 260.0 | 280.0 | 250/260 | 260/280 |
| 3 | Manual | A | 0.455 | 0.520 | 0.251 | 0.874 | 2.069 |

Fig.5c: Table of the UV Analysis of purified RNA Sequence (7979A777A77A9AAA99A7G99G9A9GG9G7A7G9AGAG).
Lot No. CH5-10R-31-01
Note: 1. N-2-acetyl-ribo-Guanosine-2'-TBDMS-3'-CNET Phosphoramidite was utilized in the chimera RNA Synthesis.
2. The sequence contains 2'-Fluoro C and 2'-Fluoro-U.
7 denotes 2'-Fluoro C base and #9 denote 2'-Fluoro U base.

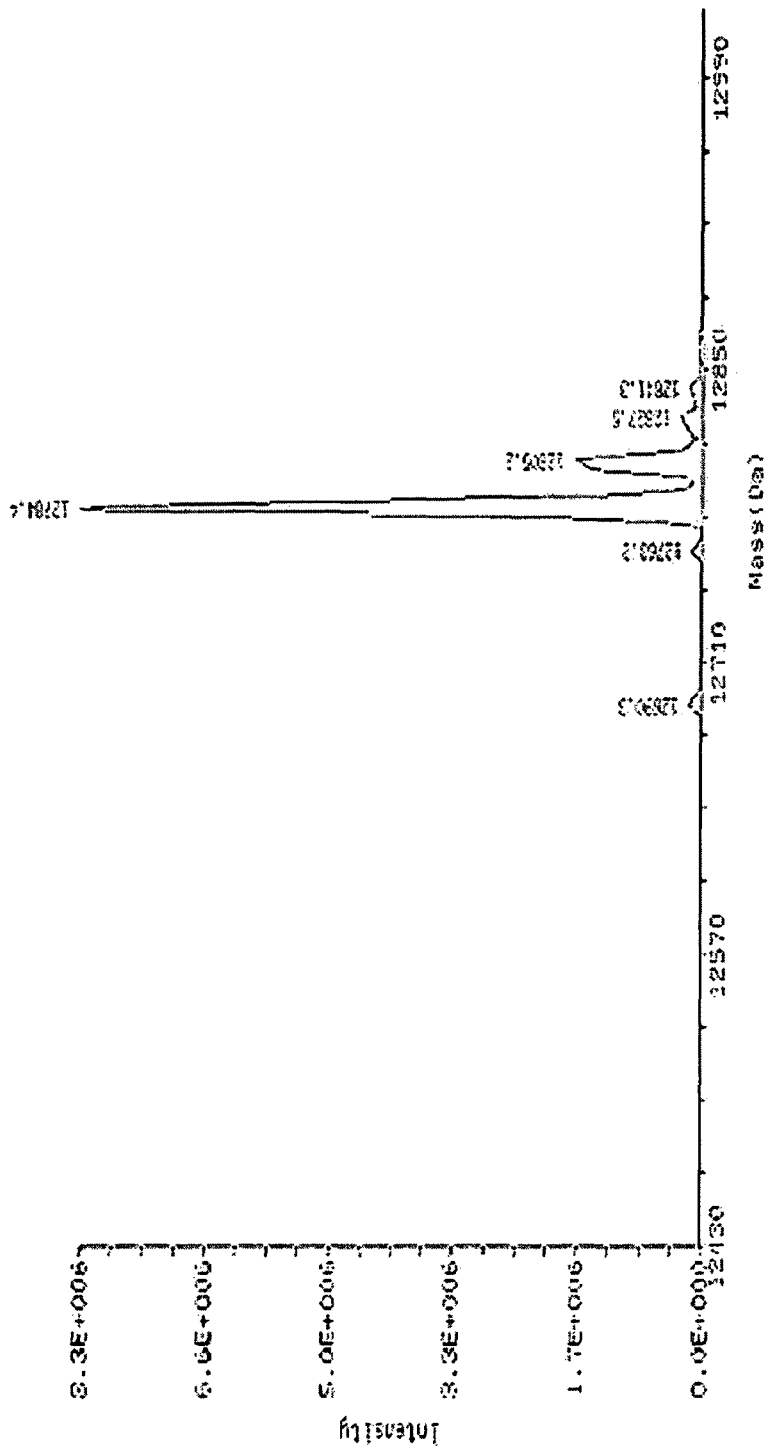
Fig.5d: ESI-MS Analysis of purified RNA Sequence (7979A777A77A9AAA99A7G99G9A9GG9G7A7G9AGAG).
Lot No. CH5-10R-31-01
Targeted mass: 12785.2
Observed Mass: 12784.4
Note: 1. N-2-acetyl-ribo-Guanosine-2'-TBDMS-3'-CNET Phosphoramidite was utilized in the chimera RNA Synthesis.
2. The sequence contains 2'-Fluoro C and 2'-Fluoro-U.
7 denotes 2'-Fluoro C base and #9 denote 2'-Fluoro U base.

Fig.5e: Synthesis Report of RNA Sequence (7979A777A77A9AAA99A7G99G9A9GG9G7A7G9AGAG).
Lot No. CH5-10R-31-01
Note: 1. N-2-acetyl-ribo-Guanosine-2'-TBDMS-3'-CNET Phosphoramidite was utilized in the chimera RNA Synthesis.
2. The sequence contains 2'-Fluoro C and 2'-Fluoro-U.
7 denotes 2'-Fluoro C base and #9 denote 2'-Fluoro U base.

Example of RNA synthesis #3:
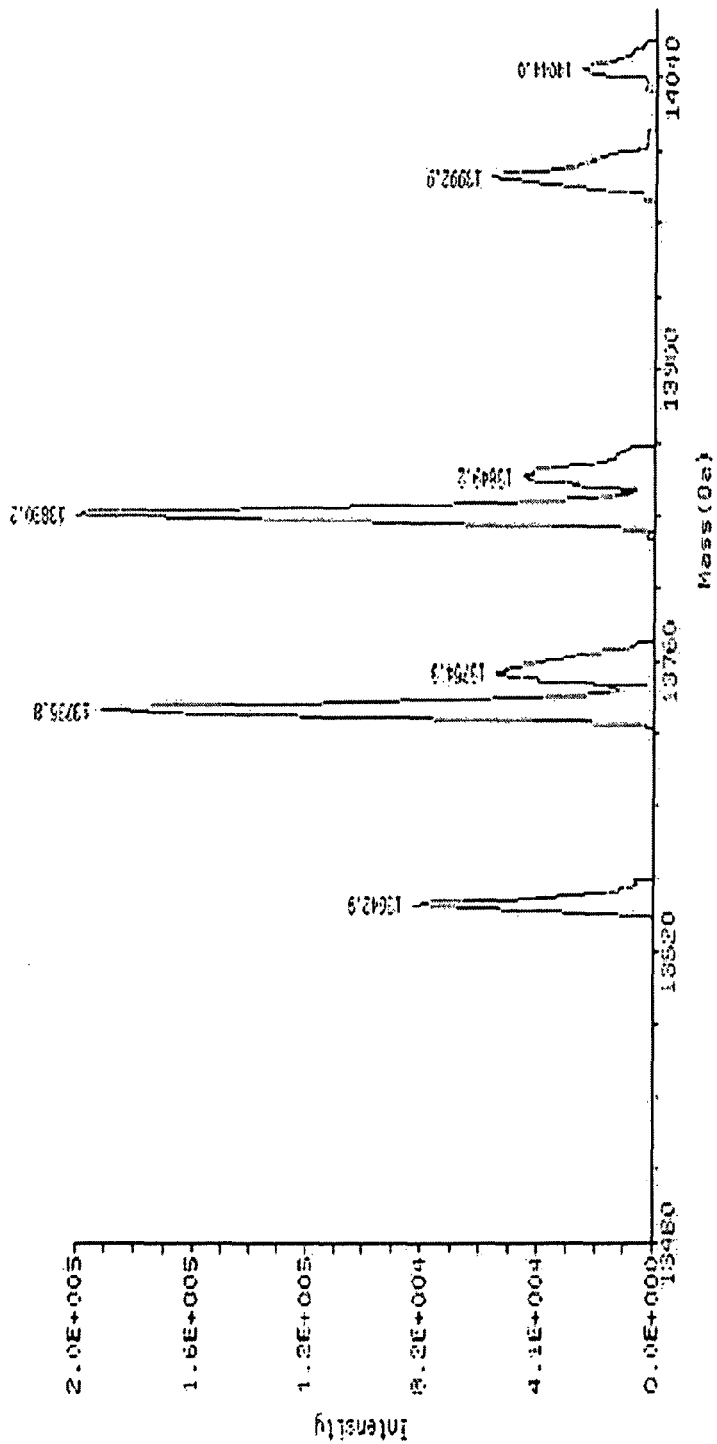
Fig.6a: ESI-MS Analysis of purified RNA Sequence (57A7GAGAG9GG97G97777AGGGGAGAA797G9G79779GG5).
Lot No. 092608
Targeted mass: 13831.7
Observed Mass: 13830.2, 13735.8, 13642.9
Note: 1. N-2-ibu-ribo-Guanosine-2'-TBDMS-3'-CNET Phosphoramidite was utilized in the chimera RNA Synthesis.
2. The sequence contains 2'-Fluoro C and 2'-Fluoro-U.
7 denotes 2'-Fluoro C base and #9 denote 2'-Fluoro U base.

Fig.6b: Synthesis Report of RNA Sequence (57A7GAGAG9GG97G9777AGGGGAGAA797G9G79779GG5).
Lot No. 092608
Note: 1. N-2-ibu-ribo-Guanosine-2'-TBDMS-3'-CNET Phosphoramidite was utilized in the chimera RNA Synthesis.
2. The sequence contains 2'-Fluoro C and 2'-Fluoro-U.
7 denotes 2'-Fluoro C base and #9 denote 2'-Fluoro U base.

SYNTHESIS OF LABILE BASE PROTECTED-MODIFIED DEOXY AND MODIFIED RIBO NUCLEOSIDES, CORRESPONDING PHOSPHORAMIDITES AND SUPPORTS AND THEIR USE IN HIGH PURITY OLIGONUCLEOTIDE SYNTHESIS

CROSS REFERENCE TO RELATED APPLICATIONS

This international application for patent claims priority from U.S. Provisional Application Ser. No. 61/216,491 entitled "Synthesis of N-2-Acetyl guanine-deoxy nucleosides, N-2-Acetyl guanine ribo nucleosides, N-2-Acetyl guanine-modified deoxy & ribo nucleosides, the corresponding phosphoramidites and their use in high purity oligonucleotide synthesis" by the same inventors filed on May 18, 2009. The entire contents of the related provisional application are herein incorporated by reference.

FIELD OF THE INVENTION

This invention relates to synthesis of novel N-2-acetyl protected deoxy and ribo-guanosine, —N-acetyl protected modified guanosine, their succinates, phosphoramidites, corresponding solid supports that are suitable for high purity DNA and RNA synthesis, and it leads to a novel approach to obtain highest purity oligonucleotides. This invention is directed to the synthesis of high purity large scale oligonucleotide synthesis.

BACKGROUND OF THE INVENTION

The chemical synthesis of oligonucleotides of DNA fragments is performed efficiently by the phosphoramidite chemistry, and the coupling reaction gives excellent yield on various solid supports (Oligodeoxy nucleotide synthesis, Phosphoramidite Approach, Serge L. Beaucage in Protocols For OLigonucleotides and Analogs, Synthesis and Properties, Editor, Sudhir Agarwal, Humana Press, 1993). Similarly excellent protocols have been developed for the synthesis of RNA, and various biologically active tRNA molecules (Oligoribonucleotide synthesis, The Silyl Phosphoramidite Method, Masad J. Damha and Kevin K. Ogilvie in Protocols For Oligonucleotides and Analogs, Synthesis and Properties, Editor, Sudhir Agarwal, Humana Press, 1993). A large number of such biologically functional DNA and RNA molecules carry base labile and modified nucleosides which cannot sustain prolonged basic conditions, generally required during deprotection. Thus dihydrouridine present in tRNA requires very mild deprotection conditions, otherwise it is completely decomposed and the quality of synthetic tRNA will be compromised. (C. Chaix, D. Molko and R. Teoule, Tetrahedron Letters, 30, 1, 711-74, 1989). In order to develop protecting groups which are milder in nature have been developed in recent past. Thus 2-(acetoxy-methyl)benzoyl (AMB) group has been reported which uses potassium carbonate as mild deprotecting group for their removal (W. H. A. Kuijpers, J. Huskens and C. A. A. Van Boeckel, Tetrahedron Lett., 31, 6729-6732, 1990) & W. H. A. Kuijpers, E. Kuyl-Yeheskiely, J. H. Van Boom and C. A. A. Van Boeckel, Nucl. Acids Res., 21, 3493-3500, 1993). The AMB group seems attractive, however there are many practical problems in their use. FMOC group was reported for the protection of amino function of 2'-deoxycytidine, 2'-deoxy adenosine and 2'-deoxy guanosine and for the corresponding ribonucleosides (H. Heikkila and J. Chattopadhyaya, Acta Chem. Scand. B 37, No. 3, 263-265, 1983). FMOC as n-protecting group as pointed out by these authors for their capability to get cleaved under very mild alkaline deprotection condition, or by bases capable to carry out selective deprotection via B-elimination of FMOC group (scheme 1). It is therefore not surprising that other attempts to synthesis of N-FMOC protected nucleoside and phosphoramidites have been carried out. The publication (R. K. Gaur, V. Bobde, M. Atreyi and K. C. Gupta, Indian Journal of Chemistry, 29B, 108-112, 1990), reports preparation of 5'-DMT-n-FMOC-dA (structure 1) and 5'-DMT-n-FMOC-dC (structure 2). However these authors could not synthesize 5'-DMT-N-FMOC-dG (structure 5). Further only p-methoxy phosphoramidites of 5% DMT-n-FMOC-dC (structure 3) and 5'-DMT-n-FMOC d A (structure 4) were synthesized by these authors. The p-methoxy phosphoramidites have only limited application in oligonucleotide synthesis. Further, no N-FMOC protected solid supports were reported.

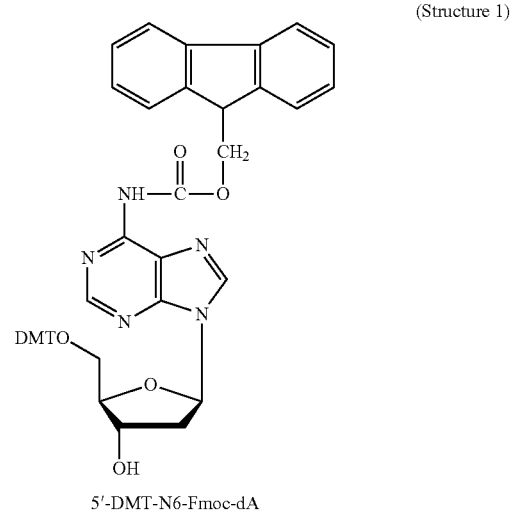

(Structure 1)

5'-DMT-N6-Fmoc-dA

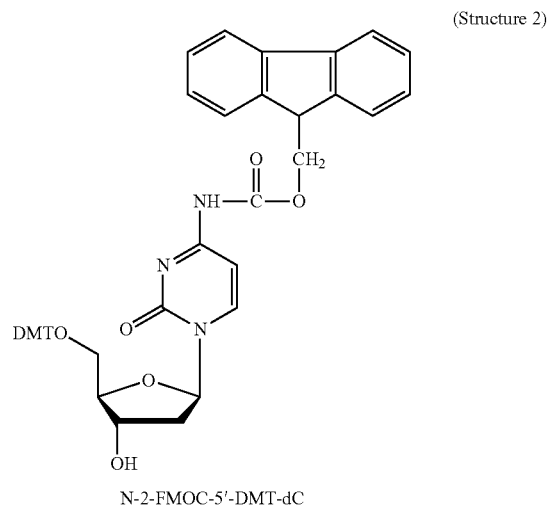

(Structure 2)

N-2-FMOC-5'-DMT-dC

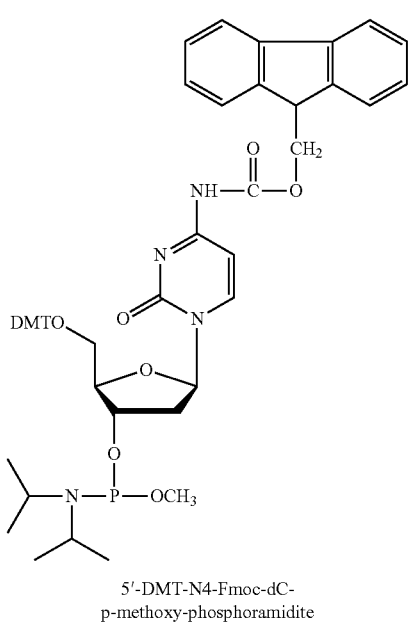

5′-DMT-N4-Fmoc-dC-
p-methoxy-phosphoramidite

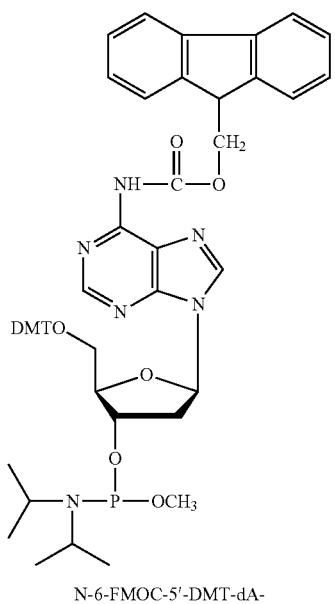

N-6-FMOC-5′-DMT-dA-
p-methoxy-phosphoramidite

The synthesis of N-FMOC-5′-DMT-dG (structure 5) had eluded so far till our present invention.

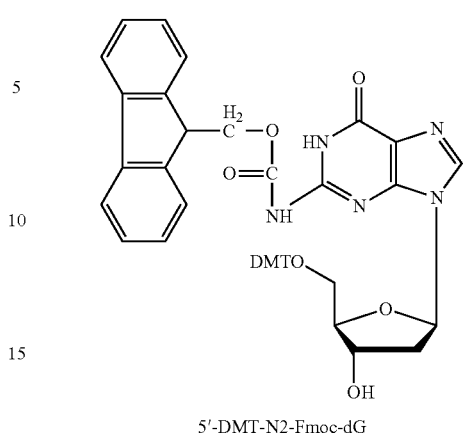

5′-DMT-N2-Fmoc-dG

Similarly no solid supports or the succinates of the N-FMOC-5′-DMT-deoxy bases (dA and dC) revealed by these other authors. Hence there is no information as to the applicability of DMT-N-6-FMOC-dA-3′-succinyl-support, which would validate the concept that the solid support containing N-6-Fmoc-dA solid supports are expected to minimize or dramatically reduce formation of N-1, i.e. depurination of 3′-dA base products during oligo synthesis and hence about the quality of the synthesized 2′-deoxy oligonucleotides. The FMOC protected nucleoside products improve the quality of the terminal 3′-dA containing oligonucleotides.

There seem to be no further attempts to make 5′-DMT-N-FMOC dG or the ribonucleoside containing N-Fmoc protected RNA synthesis synthons and the corresponding cyanoethyl phosphoramidites. The cyanoethyl phosphoramidite chemistry in DNA and RNA are currently used in present state of the art in this technology.

It was demonstrated by the authors (J. Heikkila and J. Chattopadhyaya, Acta Chem. Scand. B 37, No. 3, 263-265, 1983) that deprotection of FMOC protecting group can be carried out under various very mild basic reaction conditions. It is possible to utilize either aq ammonia condition deprotection, which results in nucleophilic displacement of FMOC protecting group, or by a Non-nucleophilic base such as triethylamine, which causes B-elimination of FMOC-active hydrogen group (scheme 1). These authors however similarly did not pursue the n-FMOC protecting group for further exploration and carried out investigation of other protecting groups such as ortho-nitro phenyl sulfenyl protected nucleosides (Structure 6).

The FMOC protecting group is very well established in peptide synthesis and one of the preferred reagents for amino group protection of alpha-amino group of amino acids for step wise peptide synthesis (Carpino, L. A., and Han, G. Y., J. Amer. Chem. Soc., 92, 5748, 1970). But Heikkila and Chattopadyaya (J. Heikkila and J. Chattopadhyaya, Acta Chem. Scand. B 37, No. 3, 263-265, 1983), who initially synthesized the FMOC deoxy and ribo nucleosides switched to (J. Heikkila, N. Balgobin and J. Chattopadhyaya, Acta Chem. Scand B 37, 857-864, 1983) to another N-protecting group, 2-nitrophenyl sulfenyl (Nps) for the protection of amino function of cytidine, adenosine, guanosine and the corresponding 2′-deoxy ribo nucleosides (structure 6).

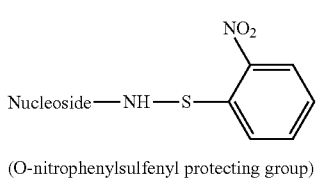

(Structure 6)

(O-nitrophenylsulfenyl protecting group)

Scheme 1. Fmoc-B-Elimination scheme

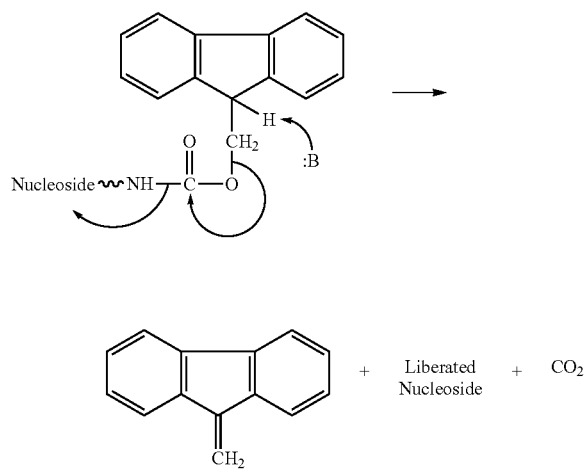

+ Liberated Nucleoside + $CO_2$

It is well known that cyanoethyl protecting group for internucleotide phosphate is eliminated by B-elimination mechanism leading to acrylonitrile and phosphodiester oligonucleotides. (scheme 2).

Scheme 2. Elimination of cyanoethyl phosphate group

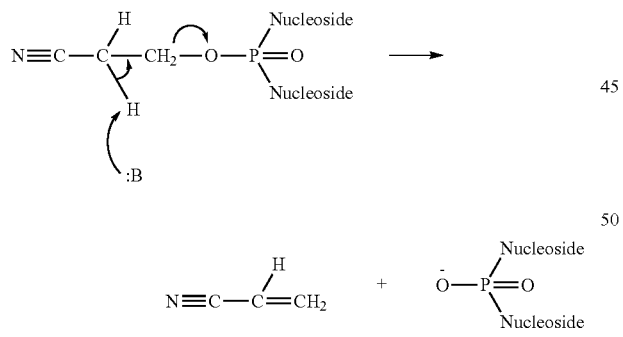

It is therefore possible to modulate the FMOC protecting group removal conditions from oligonucleotides, and the FMOC as base protecting group can be removed by the process of B-elimination, just like the B-elimination process to remove cyanoethyl group.

This process therefore offers very attractive potential to use ammonia free oligo synthesis. This process, furthermore, has potential to offer deoxyoligonucleotides for complete deprotection of oligos on solid supports. This technology or process has the potential to offer ribonucleotides such as those required for chip based technology as well high purity oligonucleotides for microRNA, Si RNA, RNA chips This group, in conjunction with cyanoethyl phosphate protecting group, therefore offers opportunity to remove both FMOC and cyanoethyl groups from the synthesized deoxy and ribo oligonucleotides on the support cleanly, preferably with non aq bases, and on support for many diagnostics application.

Our present invention is revealed by structures such as 7-10 below.

The present inventors recently proposed to utilize N-FMOC protected purine and pyrimidine bases for the Sythesis of protected Deoxy nucleosides, ribonucleosides, phosphoromidites and their use in the synthesis of oligonucleotides. Although the FMOC protecting group presents tremendous advantage, practical large scale synthesis is inconvenient and difficult to achieve in order to produce large quantities of therapeutic grade RNA or RNA chimeras having sensitive groups such as 2'-fluoro group. It is also significantly labile so that this group has a tendency to fall off and lead to byproducts or impurities. We therefore turned our attention to N-2-acetyl as guanine base protecting group. This group is significantly more stable than FMOC protecting group. Yet is quite labile as compared to isobutyryl group at N-2 position.

Our results of RNA synthesis show that quality of RNA's suffer heavily if in the automated RNA synthesis on DNA/RNA synthesizer, DMT-N-2-isobutyryl guanosine-2'-TBDMS-3'-Cyanoethyl phosphoramidite is utilized. The currently utilized, most popular and industry standard N-2-amino protecting group for guanine bases is isobutyryl. On the other hand, if DMT-N-2-acetyl guanosine-2'-TBDMS-3'-Cyanoethyl phosphoramidite (structure 6) is used, high quality of RNA's are obtained. This has been substantiated by oligonucleotide Mass spectral data presented in the present invention.

The deprotection kinetics of N-2 acetyl guanine in a nucleoside or oligonucleotide is significantly faster as compared to standard N-2 isobutyryl group on guanine residue, so that the quality of oligonucleotides especially RNA and modified RNA increases dramatically.

Synthons for RNA Synthesis (Structure 6)

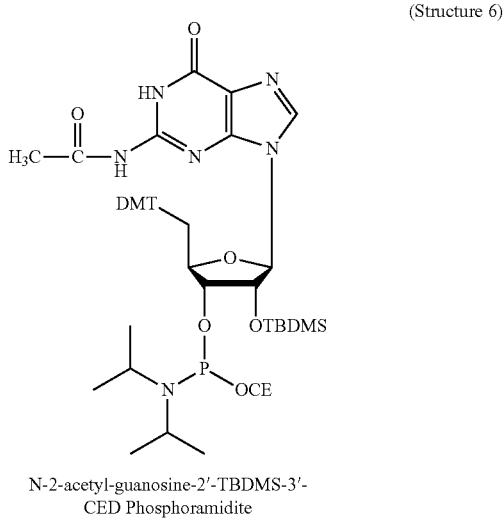

N-2-acetyl-guanosine-2'-TBDMS-3'-CED Phosphoramidite

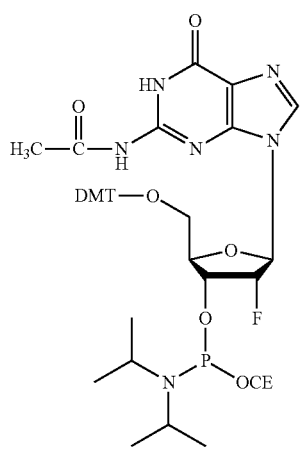

N-2-acetyl-guanosine-2'-fluoro-3'-
CED Phosphoramidite

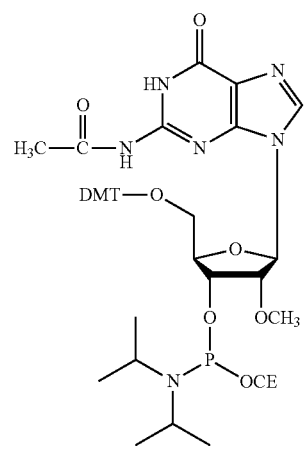

N-2-acetyl-guanosine-2'-Omethyl-3'-
CED Phosphoramidite

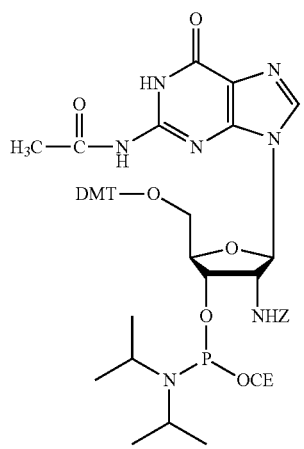

(N-2-acetyl-guanosine-2'-amino-3'-
CED Phosphoramidite); where Z is protecting group

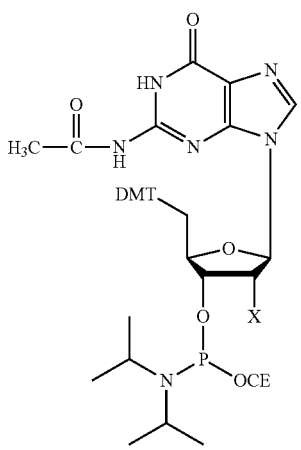

N-2-acetyl-guanine-2'-modified-3'-
CED Phosphoramidite
(Where X; F, OCH3, NH_Protected)

Scheme 1: Step wise synthesis of Synthons (structures 6) starting from compound 10, followed by 11, followed by compound 12 & 13, for RNA Synthesis:

The synthesis of phosphoramidites, structures 6 was carried out using nucleosides 10, 11, 12 & 14 as depicted by the following structures:

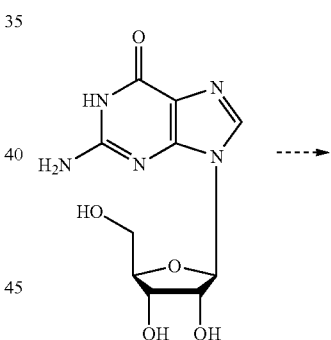

Structure 10 (Guanosine)

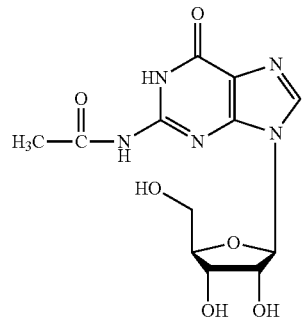

Structure 11 (N-2-acetyl-Guanosine)

9
-continued

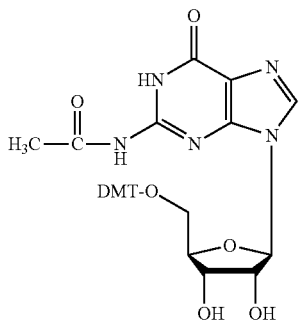

(N-2-acetyl guanosine-5'-DMT)

(Structure 13)

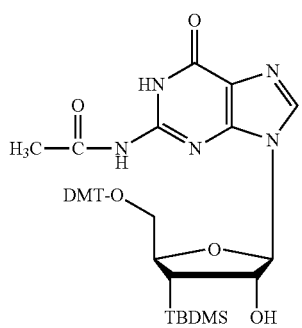

(N-2-acetyl guanosine-5'-DMT-
3'-TBDMS)

(Structure 14)

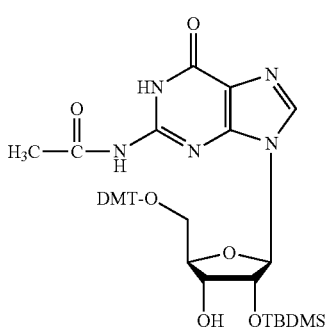

(N-2-acetyl guanosine-5'-DMT-
2'-TBDMS)

Note: compound (structure 12) is achieved by transient N-2 protected with acetyl chloride in presence of TMS Chloride/ pyridine as standard reaction conditions.

Structure 12

Scheme 2: Stepwise synthesis of Synthons (stuctures 7a, 8 & 9) for RNA Synthesis:

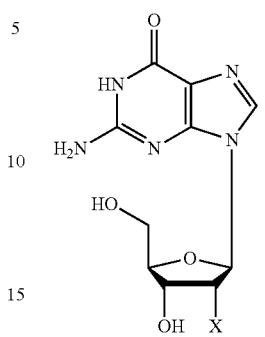

(Structure 15)
(modified guanosine-2'-X;
where X; F, OCH3, NH-
protected)

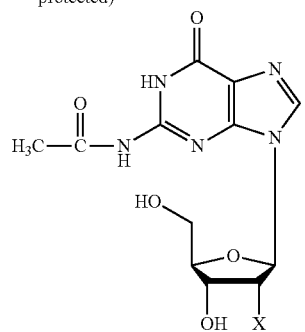

(Structure 16)
(N-2-acetyl guanosine-2'-X;
where X; F, OCH3 and NH-protected)

Note: Compound (structure 16) is produced by transient N-2 protected with acetyl chloride in presence of TMS Chloride/pyridine as standard reaction conditions.

(N-2-acetyl guanosine-5'-DMT-2'-X;
where X; F, OCH3, and NH-protected) 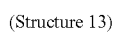 (structure 16)

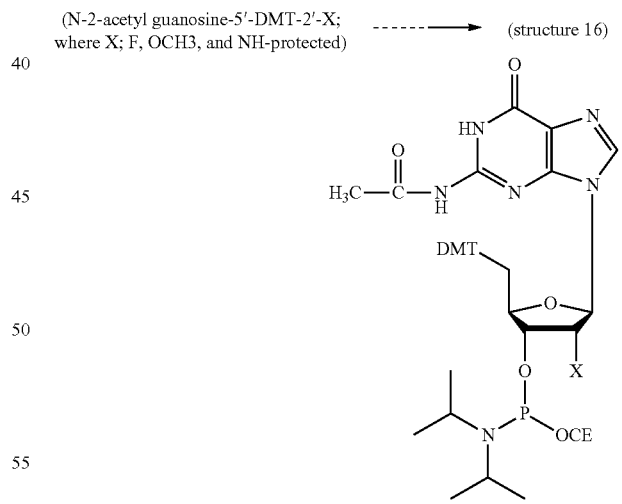

(Structure 7b)
(N-2-acetyl guanosine-5'-DMT-2'-X;
where X; F, OCH3, NH-protected-3'-
phosphoramidite)

The utility of N-FMOC protected nucleoside was discovered by the present inventors and it was shown to possess additional significance and importance. When oligo ribonucleotide chimeras comprise of mixed bases composed of 2'-fluoro and 2'-ribo bases they present a challenge in obtaining pure chimera oligonucleotides. It has been well documented by several recent reports that oligonucleotide chimeras having 2'-fluoro-2;'-deoxy bases along with natural ribo bases present difficulty in obtaining pure oligos. It has been shown that with strongly basic conditions, there is significant loss of fluorine as loss of Hydrogen Fluoride ("HF") is seen as M-20 peak in Mass spectral analysis. Besides it has also been shown that uracil and cytosine are eliminated to a significant extent, when oligo chimeras containing 2'-fluoro-2'-deoxy uridine and 2'-fluoro-2'-deoxy cytidine are part of chimeras (see scheme 3).

Scheme 3. Graphic Representation of effect on quality of oligonucleotides containing 2'-fluoro nucleosides: (a) deprotection using methyl amine, the usual deprotection condition of protecting groups of bases, (b) loss of fluorine leading to loss of HF, generating significant amount of M-20, (c) loss of cytosine and uracil, the pyrimidine bases is observed quite frequently, d) with the loss of pyrimidine, subsequent cleavage of chain occurs.

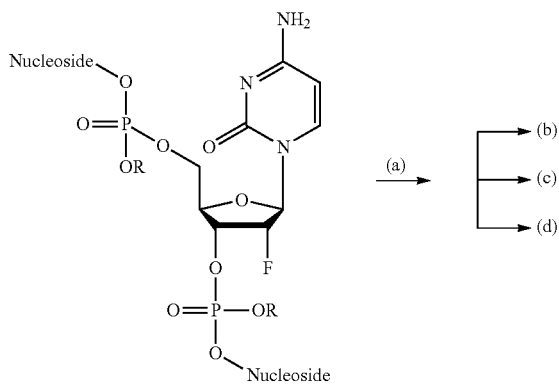

The studies as shown in scheme 3 were carried out independently by two groups recently. Ken Hill, Agilent Technologies, Boulder, Colarado; Identification of Process Related Impurities—Understanding Oligonucleotide Production, TIDES 2007, Las Vegas. Nev. The author showed depyrimidation of chimera oligonucleotides carrying 2'-fluoro-2'-deoxy pyrimidine in RNA's; and, Nanda D. Sinha, Avecia Biotechnologies Inc., Massachusetts—Depyrimidation, as well as loss of HF and chain cleavage in chimeras having 2'-fluoro-2'-deoxy pyrimidines in RNA sequences. Eurotides, 2005, Munich, Germany.

Our data shows that by utilizing n-acetyl-guanine protected ribonucleoside phosphoramidites, used in oligo with 2'-fluoro substitution, high quality full length RNA were obtained.

It is therefore imperative to utilize 2'-fluoro-2'-deoxy nucleosides and corresponding phosphoramidites with guanine protecting groups having N-2 acetyl guanine for mild and shorter base deprotection protocol. Although there is no B-elimination pathway for N-2-acetyl guanosine protecting group, still high purity and integrity oligo chimeras is obtained and RNA high quality for therapeutic and diagnostic applications, such as for applications in SiRNA synthesis.

Besides the 2'-fluoro nucleosides, 2'-O-alkyl nucleoside phosphoramidites are extensively used in the design of biologically active oligonuceotides for therapeutic and diagnostic applications as fully alkylated or as chimeras. Amongst the 2'-O-alkyl nucleosides and phosphoramidites the most common are 2'-O-Methyl oligonucleotides which have shown enormous promise in drug design and specific diagnostics applications. Thus 2'-Omethyl oligoribonucleotides-RNA complexes have higher Tm than corresponding oligo-deoxy ribonucleoside—RNA duplexes, Iribarren, A. M., Sproat, B. S., Neuner, P., Sulston, I., Ryder, U., and Lamond, A. I., Proc. Natl. Acad. Sci. USA 87, 7747-7751, 1990. Various 2'-OMethyl-N-FMOC protected nucleosides and phosphoramidites offer great advantage to produce high quality of DNA-RNA oligonucleotides and chimera for biological applications.

Defined sequence RNA synthesis is now well established and currently in use for synthesis and development of vast variety of therapeutic grade RNA aptamers, tRNA's, Si RNA and biologically active RNA molecules. This approach utilizes a ribonucleoside with suitable N-protecting group, 5'-Protecting group, generally, and most popular being dimethoxytriphenyl, commonly called DMT group, 2'-protecting group, out of which most popular is t-Butyldimethylsilyl ether and a 3'-phosphoramidite, wherein the most popular still is cyanoethyl diisopropyl (component 1). This component is then coupled with a nucleoside with a suitable N-protecting group, 2' or 3' succinate of a ribonucleoside attached to a solid support. The coupling of component 1 and 5'-OH-n-protected-2',3'-protected-nucleoside are also achieved in solution phase in the presence of an activator to lead to dimers and oligoribonucleotides, followed by oxidation (3'→5' direction synthesis), also lead to protected dinucleoside having a 3'-5'-internucleotide linkage, Ogilvie, K. K., Can. J. Chem., 58, 2686, 1980.

The N-acetyl guanine protecting group offers great potential in RNA synthesis of defined sequence based on our invention as outlined here.

This group can be utilized in conjunction with various 2'-protecting groups required for RNA synthesis. The most widely utilized 2'-protecting, tert-butyl-dimethylsilyl, which has been extensively developed by Ogilvie and coworkers as 2'-hydroxy protecting group for oligo ribonucleotide synthesis (Ogilvie, K. K., Sadana, K. L, Thompson, E. A., Quilliam, M. A., and Westmore, J. B *Tetrahedron Letters*, 15, 2861-2864, 1974; Ogilvie, K. K., Beaucage, S. L, Entwistle, D. W., Thompson, E. A., Quilliam, M. A., and Westmore, J. B. *J. Carbohydrate Nucleosides Nucleotides*, 3, 197-227, 1976; Ogilvie, K. K. Proceedings of the 5th International Round Table on Nucleosides, Nucleotides and Their Biological Applications, Rideout, J. L., Henry, D. W., and Beacham L. M., III, eds., Academic, London, pp. 209-256, 1983).

These studies subsequently led to continued developments of methods which were amenable to both solution and solid phase oligonucleotide synthesis, and the first chemical synthesis of RNA molecules of the size and character of tRNA (Usman, N., Ogilvie, K. K., Jiang, M.-Y., and Cedergren, R. J. *J. Am. Chem. Soc.* 109, 7845-7854, 1987; Ogilvie, K. K., Usman, N., Nicoghosian, K, and Cedergren, R. J. *Proc. Natl. Acad. Sci. USA*, 85, 5764-5768, 1988; Bratty, J., Wu, T., Nicoghosian, K., Ogilvie, K. K., Perrault, J.-P., Keith, G. and Cedergren, R., *FEBS Lett.* 269, 60-64, 1990). The literature has been amply reviewed in subsequent excellent publication: Gait, M. J., Pritchard, C. and Slim, G., Oligonucleotides and Their Analogs: A Practical Approach (Gait, M. J., ed.), Oxford University Press Oxford, England, pp 25-48, 1991. Other protecting groups which have been lately employed for RNA synthesis are; bis(2-acetoxyethyloxy)methyl (ACE), Scaringe, S. A., Wincott, F. E., Caruthers, M. H., J. Am. Chem. Soc., 120: 11820-11821, 1998; triisopropylsilyloxy methyl (TOM), Pitsch, S., Weiss, P. A., Jenny, L., Stutz, A., Wu, X., Helv. Chim. Acta. 84, 3773-3795, 2001 and t-butyldithiomethyl (DTM) (structure 16), Semenyuk, A., Foldesi, A., Johansson, T., Estmer-Nilsson, C., Blomgren, P., Brannvall, M., Kirsebom, L. A., Kwiatkowski, M., J. Am. Chem. Soc., 128: 12356-12357, 2006 have been introduced.

Recently the scientists at ChemGenes have developed the method of RNA synthesis in reverse direction (5'→3' direction), for efficient incorporation of many ligands and chromophores conveniently and efficiently at the 3'-end of RNA molecules and a recent publication, Srivastava, S. C., Pandey, D. P., Srivastava, N., Bajpai, S. P., Nucleic Acids Symposium Series No. 52, 103-104, 2008 (structure 20, 21 & 22). Appropriately N-acetyl protected guanine can nucleosides, deoxy and ribo are envisaged to be synthesized and DNA and RNA synthesis is proposed to utilize the benefits which reverse DNA and RNA synthesis offer. (US patent application entitled "RNA Synthesis—Phosphoramidites for Synthetic RNA in the Reverse Direction, and Application in Convenient Introduction of Ligands, Chromophores and Modifications of Synthetic RNA at the 3'-End" by Suresh C. Srivastava et al. filed on Sep. 8, 2009, and US patent application entitled "Synthesis of N-Fmoc Protected Deoxy Nucleosides, Ribo Nucleosides . . . " by Srivastava et al. filed on Nov. 30, 2009)

A novel 2'-protecting group, acetal levulinyl ester (ALE) (structure 15 has been recently proposed (J. G. Lackey and M. J. Damha, Nucleic Acids Symposium Series, No. 52, 35-36, 2008). Similar to this protecting group another 2'-labile protecvting group based on similar chemical nature, 2'-O-acetal ester, pivaloyloxy methyl which has been found mild 2'-O protercting group, T. Lavergne, A. Martin, F. Debart, J-J Vasseur, Nucleic Acids Symposium Series No. 52-51-52, 2008. The base protecting group used by these authors was n-acetyl and tbPAC. This gives additional credence to our process. And n-acetyl for RNA synthesis with other 2'-protecting groups or 2'-modification would be an ideal group for deprotection under mild basic condition in shorter period of time.

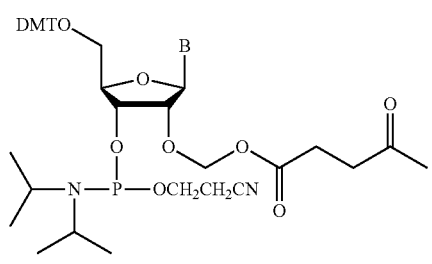

2'-O-ALE-N-Fmoc amidites (Structure 17)

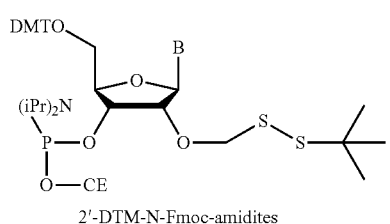

2'-DTM-N-Fmoc-amidites (Structure 18)

Chemically modified RNA have been synthesized having modified arabino sugars, 2'-deoxy-2'-fluoro-beta-D_arabinonucleic acid (FANA; structure 17)) and 2'-deoxy-4'-thio-2'-fluoro-beta-D_arabinonucleic acid (4'-Thio-FANA; structure 18) into sequences for SiRNA activities, Dowler, T., Bergeron, D., Tedeschi, Anna-Lisa, Paquet, L., Ferrari, N., Damha, M. J., Nucl. Acids Res., 34, 1669-1675, 2006. Amongst several new 2'-protecting group chemistry which have been developed, the 2'-protecting 2-cyanoethoxymethyl (CEM) (structure 19) has been shown for producing very long RNA also carries out RNA synthesis in conventional (3'→5' direction). However the quality of these long RNA remain in question.

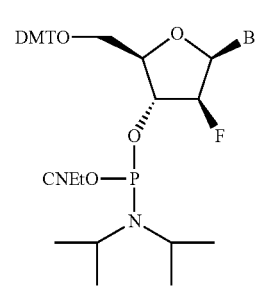

2'-F-ANA modified phosphoramidites phosphoramidites (Structure 19)

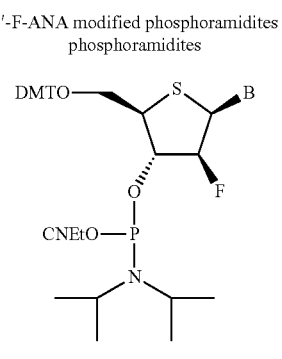

4'-Thio-2'-F-ANA modified (Structure 20)

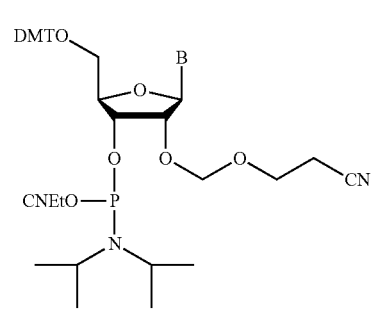

2'-CEM Protected RNA Intermediates (Structure 21)

The N-acetyl protected guanine as nucleoside base having the 2'-protecting group discussed above can be combined and utilized in high purity RNA synthesis. The N-acetyl guanine protected nucleoside offers great potential in RNA synthesis of defined sequence. This applies to RNA synthesis in the conventional direction (3'→5' direction as well as using our newly discovered 5'→3' direction synthons; structures 21, 22 & 23).

Structures of Reverse Phosphoramidites and Solid Supports:

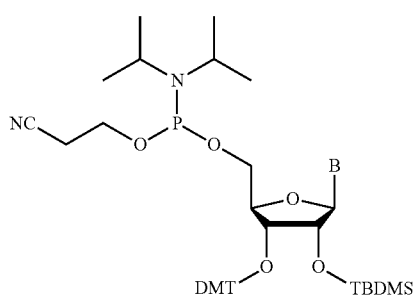

Reverse RNA synthon-2'-tBDSilyl-3'-DMT-5'-CED amidite (Structure 22)

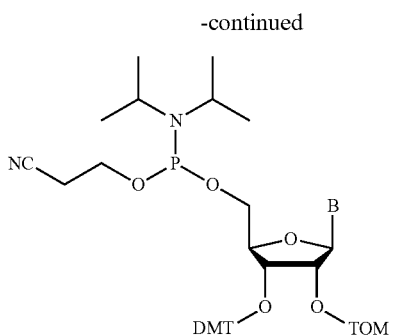

Reverse RNA synthon-2'-TOM-3'-DMT-5'-CED amidite (Structure 23)

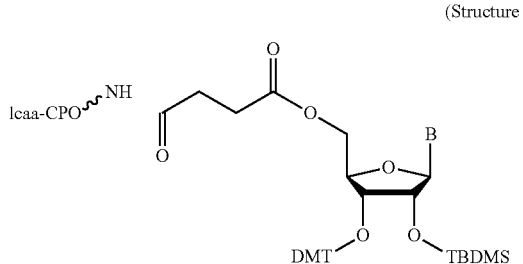

Reverse RNA synthon 2'-tBDMS-3'-DMT-5'-succinyl Support
Where B = A (N-Bz), C (N-Bz), C (N-Ac), G (N-Ac), U.

(Structure 24)

Chemical synthesis of RNA is desirable because it avoids the inefficiencies and limitation of scale of synthesis such as by in vitro transcription by T7 RNA polymerase, Helm, M., Brule, H., Giege, R., Florence, C., RNA, 5:618-621, 1999. Chemical synthesis of RNA is desirable for studies of RNA structure and function, and many useful modifications can be achieved selectively, such as site specific introduction of functional groups; viz., disulphide cross linking as a probe of RNA tertiary structures, Maglott, E. J., Glick, G. D., Nucl. Acids Res., 26: 1301-1308, 1999. Synthesis of long RNA is very important for biologically active molecules such as tRNA, and such synthesis have been achieved, Persson, T., Kutzke, U., Busch, S., Held, R., Harmann, R. K., Bioorgan. Med. Chem., 9:51-56, 2001; Oglvie, K. K., Usman, N., Nicoghosian, K., Cedrgren, R. J., Proc. Natl. Acad. Sci., USA, 85:5764-5768, 1988; Bratty, J., Wu, T., Nicoghosian, K., Ogilvie, K. K., Perreault, J.-P., Keith, G., Cedergren, R. J., F.E.B.S. Lett., 269:60-64, 1990; Gasparutto, D., Livache, T., Bazin, H., Duplaa, A. M., Guy, A., Khorlin, A., Molko, D., Roget, A., Teoule, R., Nucl. Acids. Res., 20:5159-5166, 1992; Goodwin, J. T., Stanick, W. A., Glick, G. D., J. Org. Chem., 59:7941-7943, 1994. The aforementioned techniques cited in this para, employ synthesis of RNA in reverse direction (5'→3' direction), and hence introduction of a number of groups required for selective introduction at 3'-end is practical and convenient. We have observed higher coupling efficiency per step during automated oligo synthesis with our reverse RNA amidites (structures 21, 22, 23), and therefore they have greater ability to get higher purity and produce very long oligos. We also demonstrated that the process of our invention leads oligonucleotide free of M+1 species. Such species lead to closer impurities as shoulder of desired peak during HPLC analysis or purification or Gel purification. Such reverse RNA structures replacing the standard n-protecting group with n-FMOC protecting group offer additional advantages not previously foreseen.

This invention relates to novel synthesis methodology utilizing N-acetyl guanine protected nucleosides, succinates, phosphoramidites, corresponding solid supports that are suitable for oligo deoxy nucleosides and RNA oligonucleotide synthesis. Our discovery using N-acetyl as nucleoside base protecting group, which is more base labile protecting group as compared to n-isobutyryl group is a novel approach to obtain highest purity oligonucleotides. This approach is designed to lead to very high purity and very clean oligonucleotide, after removal of the protecting groups and efficiently in order to produce high purity and therapeutic grade DNA oligonucleotides, RNA oligonuicleotides, diagnostic DNA, diagnostic RNA for microarray platform. The deprotection of acetyl protecting groups of the natural deoxy and ribonucleosides occurs under the mild deprotection and shorter contact time deprotection conditions and removal of such groups under very mild conditions would allows synthesis of various DNA and RNA of highest purity for diagnostics and therapeutic application. This approach is further designed to use acetyl guanine protecting group on various base sensitive nucleoside, and for use in oligo peptide synthesis.

Defined sequences RNA synthesis is now well established and currently in use for synthesis and development of vast variety of therapeutic grade RNA aptamers, tRNA's, Si RNA and biologically active RNA molecules. This approach utilizes a ribonucleoside with suitable N-protecting group, 5'-Protecting group, generally and most popular being dimethoxytriphenyl, commonly called DMT group, 2'-protecting group, out of which most popular being t-Butyldimethylsilyl ether and a 3'-phosphoramidite, the most popular being cyanoethyl diisopropyl (component 1). This component is then coupled with a nucleoside with a suitable N-protecting group, 2' or 3' succinate of a ribonucleoside attached to a solid support (component 2). The coupling of component 1 and 5'-OH-n-protected-2',3'-protected-nucleoside (component 3) are also achieved in solution phase in presence of an activator to lead to dimers and oligoribonucleotides, followed by oxidation (3'→5' direction synthesis), also lead to protected dinucleoside having a 3'-5'-internucleotide linkage, Ogilvie, K. K., Can. J. Chem., 58, 2686, 1980.

For the N-acetyl guanine nucleoside protecting group the widely utilized 2'-protecting group, viz.; TBDMS group, which has been extensively developed by Ogilvie and coworkers as 2'-hydroxy protecting group for oligo ribonucleotide synthesis (Ogilvie, K. K., Sadana, K. L, Thompson, E. A., Quilliam, M. A., and Westmore, J. B Tetrahedron Letters, 15, 2861-2864, 1974; Ogilvie, K. K., Beaucage, S. L, Entwistle, D. W., Thompson, E. A., Quilliam, M. A., and Westmore, J. B. *J. Carbohydrate Nucleosides Nucleotides,* 3, 197-227, 1976; Ogilvie, K. K. Proceedings of the 5th International Round Table on Nucleosides, Nucleotides and Their Biological Applications, Rideout, J. L., Henry, D. W., and Beacham L. M., III, eds., Academic, London, pp. 209-256, 1983).

These studies subsequently led to continued developments of methods which were amenable to both solution and solid phase oligonucleotide synthesis, and the first chemical synthesis of RNA molecules of the size and character of tRNA (Usman, N., Ogilvie, K. K., Jiang, M.-Y., and Cedergren, R. J. *J. Am. Chem. Soc.* 109, 7845-7854, 1987; Ogilvie, K. K., Usman, N., Nicoghosian, K, and Cedergren, R. J. Proc. Natl. Acad. Sci. USA, 85, 5764-5768, 1988; Bratty, J., Wu, T., Nicoghosian, K., Ogilvie, K. K., Perrault, J.-P., Keith, G. and Cedergren, R., *FEBS Lett.* 269, 60-64, 1990). The literature has been amply reviewed in subsequent excellent publication: Gait, M. J., Pritchard, C. and Slim, G., Oligonucleotides and Their Analogs: A Practical Approach (Gait, M. J., ed.), Oxford University Press Oxford, England, pp 25-48, 1991. Other protecting groups which have been lately employed for RNA synthesis are; bis(2-acetoxyethyloxy)methyl (ACE), Scaringe, S. A., Wincott, F. E., Caruthers, M. H., J. Am. Chem. Soc., 120: 11820-11821, 1998; triisopropylsilyloxy methyl (TOM), Pitsch, S., Weiss, P. A., Jenny, L., Stutz, A., Wu, X., Helv. Chim. Acta. 84, 3773-3795, 2001 and t-butyldithiomethyl (DTM) (structure 1), Semenyuk, A., Foldesi, A., Johansson, T., Estmer-Nilsson, C., Blomgren, P., Brannvall, M., Kirsebom, L. A., Kwiatkowski, M., J. Am. Chem. Soc., 128: 12356-12357, 2006 have been introduced. However none of these are amenable to carry out the synthesis in reverse direction (5'→3' direction), and hence lack the capability of introduction of many ligands and chromophores conveniently and efficiently at the 3'-end of RNA molecules.

Our present invention is directed towards the synthesis of high purity RNA's and specifically to introduce nucleosidic or non-nucleosidic bases, which are labile in nature for synthesis of synthetic RNA's. Such RNA's will have vast application in therapeutics, diagnostics, drug design and selective inhibition of an RNA sequence within cellular environment, on demand blocking a function of different types of RNA present inside cell. Silencing gene expression at mRNA level with nucleic acid based molecules is a fascinating approach. Among these RNA interference (RNAi) has become a proven approach which offers great potential for selective gene inhibition and showing great promise for application in control and management of various biochemical and pharmacological processes. Early studies by Fire et al., Fire, A., Xu, S., Montgomery, M. K., Kostas, S. A., Driver, S. E., and Mello, C. C, Nature, 391, 806-811, 1998, showed that RNA interference in Caenorhabditis elegans is mediated by 21 and 22 nucleotide RNA sequences. This was further confirmed as general phenomenon of specific inhibition of gene expression by small double stranded RNA's being mediated by 21 and 22 nucleotide RNA's, Genes Dev., 15, 188-200, 2001. Simultaneous studies by Capie, N. J., Parrish, S., Imani, F., Fire, A., and Morgan, R. A., confirmed such phenomenon of specific gene expression by small double stranded (dS) RNAs in invertebrates and vertebrates alike. Subsequently a vast amount of research led to confirmation of above studies and established RNAi as a powerful tool for selectively and very specific gene inhibition and regulation, Nishikura, K., Cell, 107, 415-418, 2001; Nykanen, A., Haley, B., Zamore, P. D., Cell, 107, 309-321, 2001; Tuschl, T., Nat. Biotechnol., 20, 446-448, 2002; Mittal, V., Nature Rev., 5, 355-365, 2004; Proc. Natl. Acad. Sci. USA, 99, 6047-6052, 2002; Donze, O. & Picard, D., Nucl. Acids. Res., 30, e46, 2002; Sui, G., Soohoo, C., Affar el, B., Gay, F., Shi, Y., Forrester, W. c., and Shi, Y., Proc. Natl. Acad. Sci. USA, 99, 5515-5520, 2002; Paddison, P. J., Caudy, A. A., Bernstein, E., Hannon, G. J., and Conklin, D. S., Genes Dev., 16, 948-959, 2002.

SUMMARY OF THE INVENTION

The invention provides a novel method of RNA synthesis utilizing N-2-acetyl guanosine-5'-DMT-2'-TBDMS-protected nucleoside phosphoramidite and other nucleoside phosphoramidites outlined in Formula 1 below. The synthetic route that has been developed allows obtaining desired nucleosides without any contamination with unwanted impurities. The N-2-acetyl protected guanosine nucleosides and other N-2 acetyl protected nucleosides having various 2'-protecting group discussed or 2'-modification, such as 2'-fluoro or 2'-amino groups can be combined with cyanoethyl phosphate protecting group and utilized in high purity RNA synthesis

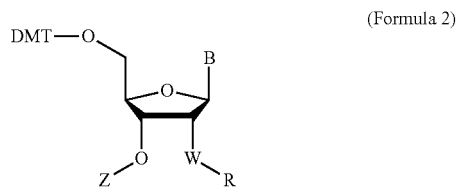

(Formula 2)

Where B=Adenine (N-bz), Cytosine (N-acetyl), Guanine (N-acetyl), 5-methyl cytosine (N-Fmoc), 5-bromocytidine (N-Fmoc), 5-iodo cytosine (N-Fmoc), 5-fluorocytosine (N-Fmoc), 2,6-diaminopurine (N-Fmoc), or 2-amino purine (N-Fmoc);

Z=succinimido long chain attached to a solid support, hydroquinone succinimido long chain spacer attached to solid support, or oxalyl amido long chain spacer attached to solid support;

W=Oxygen & R is H; or, W=Oxygen and R=tButyldimethyl silyl, TOM (triisopropyloxymethylene), acetal levulinyl ester (ALE), pivaloyloxy; cyanoethylmethylene (CEM); or dithiomethylene (DTM); or, W=oxygen and R is methyl or other higher alkyl, alkene or alkyne; or, W=ribo Fluorine, where the fluoro radical points downward in ribo configuration and R is absent; or W=ara fluorine, where the fluoro radical points upward in ara configuration (Formula 3) and R is absent; or, W=amino, and R=amino protecting group.

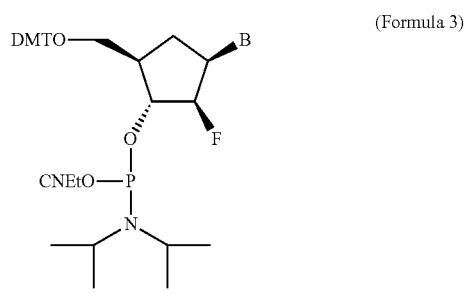

(Formula 3)

The nucleosides can be used in oligonucleotide synthesis. The base deprotection step can be performed in mild basic conditions or a tertiary amine, secondary amines, such as piperidine capable of removal of Fmoc protecting group via B-elimination in solution phase or on solid support without oligonucleotide detachment.

The invention also envisages kits that contain one or more of the disclosed nucleoside compositions.

BRIEF DESCRIPTION OF THE DRAWINGS

The drawing figures display the experimental results as follows:

FIG. 1a: HPLC Chromatogram of 5'-DMT-ribo Guanosine (n-acetyl)

FIG. 1b: UV Analysis of 5'-DMT-ribo Guanosine (n-acetyl)

FIG. 1c: Table of the UV Analysis of 5'-DMT-ribo Guanosine (n-acetyl)

FIG. 2a: HPLC Chromatogram of 5'-DMT-2'-TBDMS-ribo Guanosine (n-acetyl)

FIG. 2b: UV Analysis of 5'-DMT-2'-TBDMS-ribo Guanosine (n-acetyl)

FIG. 2c: Table of the UV Analysis of 5'-DMT-2'-TBDMS-ribo Guanosine (n-acetyl)

FIG. 3a: HPLC Chromatogram of 5'-DMT-2'-TBDMS-ribo Guanosine (n-acetyl)-phosphoramidite FIG. 3b: UV Analysis of 5'-DMT-2'-TBDMS-ribo Guanosine (n-acetyl)-phosphoramidite FIG. 3c: Table of the UV Analysis of 5'-DMT-2'-TBDMS-ribo Guanosine (n-acetyl)-phosphoramidite FIG. 3d: 31 P NMR Spectrum of 5'-DMT-2'-TBDMS-ribo Guanosine (n-acetyl)-phosphoramidite FIG. 4a: HPLC Chromatogram of purified RNA Sequence (G7799G97GAAAGA79GA9A9AGAGG7).

Lot No. CH5-9R-45-01

After purification purity: 91.3%

Note: 1. N-2-acetyl-ribo-Guanosine-2'-TBDMS-3'-CNET Phosphoramidite was utilized in the chimera RNA Synthesis.

Note: 2. The sequence contains 2'-Fluoro C and 2'-Fluoro-U.

7 denotes 2'-Fluoro C base and #9 denote 2'-Fluoro U base.

FIG. 4b: UV Analysis of purified RNA Sequence (G7799G97GAAAGA79GA9A9AGAGG7).

Lot No. CH5-9R-45-01

Note: 1. N-2-acetyl-ribo-Guanosine-2'-TBDMS-3'-CNET Phosphoramidite was utilized in the chimera RNA Synthesis.

Note: 2. The sequence contains 2'-Fluoro C and 2'-Fluoro-U.

7 denotes 2'-Fluoro C base and #9 denote 2'-Fluoro U base.

FIG. 4c: Table of UV Analysis of purified RNA Sequence (G7799G97GAAAGA79GA9A9AGAGG7).

Lot No. CH5-9R-45-01

Note: 1. N-2-acetyl-ribo-Guanosine-2'-TBDMS-3'-CNET Phosphoramidite was utilized in the chimera RNA Synthesis.

Note: 2. The sequence contains 2'-Fluoro C and 2'-Fluoro-U.

7 denotes 2'-Fluoro C base and #9 denote 2'-Fluoro U base.

FIG. 4d: ESI-MS Analysis of purified RNA Sequence (G7799G97GAAAGA79GA9A9AGAGG7).

Lot No. CH5-9R-45-01

Targeted mass: 8757.5

Observed Mass: 8756.3

Note: 1. N-2-acetyl-ribo-Guanosine-2'-TBDMS-3'-CNET Phosphoramidite was utilized in the chimera RNA Synthesis.

Note: 2. The sequence contains 2'-Fluoro C and 2'-Fluoro-U.

7 denotes 2'-Fluoro C base and #9 denote 2'-Fluoro U base.

FIG. 4e: Synthesis Report of RNA Sequence (G7799G97GAAAGA79GA9A9AGAGG7).

Lot No. CH5-9R-45-01

Note: 1. N-2-acetyl-ribo-Guanosine-2'-TBDMS-3'-CNET Phosphoramidite was utilized in the chimera RNA Synthesis.

Note: 2. The sequence contains 2'-Fluoro C and 2'-Fluoro-U.

7 denotes 2'-Fluoro C base and #9 denote 2'-Fluoro U base.

FIG. 5a: HPLC Chromatogram of purified RNA Sequence (7979A777A77A9AAA99A7G99G9A9GG9G7A7G9A-GAG).

Lot No. CH5-10R-31-01

After purification purity: 90.53%

Note: 1. N-2-acetyl-ribo-Guanosine-2'-TBDMS-3'-CNET Phosphoramidite was utilized in the chimera RNA Synthesis.

Note: 2. The sequence contains 2'-Fluoro C and 2'-Fluoro-U.

7 denotes 2'-Fluoro C base and #9 denote 2'-Fluoro U base.

FIG. 5b: UV Analysis of purified RNA Sequence (7979A777A77A9AAA99A7G99G9A9GG9G7A7G9A-GAG).

Lot No. CH5-10R-31-01

Note: 1. N-2-acetyl-ribo-Guanosine-2'-TBDMS-3'-CNET Phosphoramidite was utilized in the chimera RNA Synthesis.

Note: 2. The sequence contains 2'-Fluoro C and 2'-Fluoro-U.

7 denotes 2'-Fluoro C base and #9 denote 2'-Fluoro U base.

FIG. 5c: Table of the UV Analysis of purified RNA Sequence (7979A777A77A9AAA99A7G99G9A9GG9G7A7G9AGAG).

Lot No. CH5-10R-31-01

Note: 1. N-2-acetyl-ribo-Guanosine-2'-TBDMS-3'-CNET Phosphoramidite was utilized in the chimera RNA Synthesis.

Note: 2. The sequence contains 2'-Fluoro C and 2'-Fluoro-U.

7 denotes 2'-Fluoro C base and #9 denote 2'-Fluoro U base.

FIG. 5d: ESI-MS Analysis of purified RNA Sequence (7979A777A77A9AAA99A7G99G9A9GG9G7A7G9A-GAG).

Lot No. CH5-10R-31-01

Targeted mass: 12785.2

Observed Mass: 12784.4

Note: 1. N-2-acetyl-ribo-Guanosine-2'-TBDMS-3'-CNET Phosphoramidite was utilized in the chimera RNA Synthesis.

Note: 2. The sequence contains 2'-Fluoro C and 2'-Fluoro-U.

7 denotes 2'-Fluoro C base and #9 denote 2'-Fluoro U base.

FIG. 5e: Synthesis Report of RNA Sequence (7979A777A77A9AAA99A7G99G9A9GG9G7A7G9A-GAG).

Lot No. CH5-10R-31-01

Note: 1. N-2-acetyl-ribo-Guanosine-2'-TBDMS-3'-CNET Phosphoramidite was utilized in the chimera RNA Synthesis.

Note: 2. The sequence contains 2'-Fluoro C and 2'-Fluoro-U.

7 denotes 2'-Fluoro C base and #9 denote 2'-Fluoro U base.

FIG. 6a: ESI-MS Analysis of purified RNA Sequence (57A7GAGAG9GG97G97777AGGGGAGAA797G9G-79779GG5).

Lot No. 092608

Targeted mass: 13831.7

Observed Mass: 13830.2, 13735.8, 13642.9

Note: 1. N-2-ibu-ribo-Guanosine-2'-TBDMS-3'-CNET Phosphoramidite was utilized in the chimera RNA Synthesis.

Note: 2. The sequence contains 2'-Fluoro C and 2'-Fluoro-U.

7 denotes 2'-Fluoro C base and #9 denote 2'-Fluoro U base.

FIG. 6b: Synthesis Report of RNA Sequence (57A7GAGAG9GG97G97777AGGGGAGAA797G9G-79779GG5).

Lot No. 092608

Note: 1. N-2-ibu-ribo-Guanosine-2'-TBDMS-3'-CNET Phosphoramidite was utilized in the chimera RNA Synthesis.

Note: 2. The sequence contains 2'-Fluoro C and 2'-Fluoro-U.

7 denotes 2'-Fluoro C base and #9 denote 2'-Fluoro U base.

DETAILED DESCRIPTION OF THE INVENTION

This invention relates to synthesis of novel N-2-acetyl protected deoxy and ribo-guanosine, —N-acetyl protected modified guanosine, their succinates, phosphoramidites, corresponding solid supports that are suitable for high purity DNA and RNA synthesis. Our discovery using N-acetyl as guanine purine base protecting group, which is more base labile protecting group as compared to traditional N-2-isobutyryl guanine, is a novel approach to obtain highest purity oligonucleotides. This approach is designed to lead to high purity and very clean oligonucleotide, after efficient removal of the protecting groups and to produce high purity therapeutic grade DNA oligonucleotides, RNA oligonucleotides, diagnostic DNA, diagnostic RNA for microarray platform and high purity oligonucleotides in general. The deprotection of N-acetyl protecting groups of the natural deoxy and ribonucleosides and modified deoxy and ribonucleotides occurs during a shorter period of base treatment conditions and removal of acetyl group from guanine moieties under such conditions allows synthesis of various DNA and RNA of highest purity for diagnostics and therapeutic application, RNA synthesis anmd high quality SiRNA in general. This approach is further designed to use N-acetyl guanine protecting group on various base sensitive nucleoside such as sugar fluorinated oligo nucleotides synthesis.

The nucleic bases in our invention protected with N-2 acetyl guanine and sugar moiety in the nucleosides carry a 5'-DMT group in deoxyribonucleosides, 2'-tert butyl dimethyl silyl and 3'-cyanoethylphosphoramidite (CED) (group 1), N-2 acetyl guanine and sugar moiety in the nucleosides carry a 5'-DMT group in deoxyribonucleosides, 2'-fluoro group and 3'-cyanoethylphosphoramidite (CED) (group 2), N-2 acetyl guanine and sugar moiety in the nucleosides carry a 5'-DMT group in deoxyribonucleosides, 2'-Omethyl group and 3'-yanoethylphosphoramidite (CED) (group 3), N-2 acetyl guanine and sugar moiety in the nucleosides carry a 5'-DMT group in deoxyribonucleosides, 2'-amino (appropriately protected) group and 3'-cyanoethylphosphoramidite (CED) (group 4), 5'-DMT-3'-succinyl-Icaa CPG-N-acetyl guanine protected nucleosides or 5'-DMT-2'-tBDsilyl (tBDSi) -3'-cyanoethylphosphoramidite (CED). N-2 acetyl guanine and sugar moiety in the nucleosides carry a 5'-DMT group in deoxyribonucleosides (group 5), 5'-DMT-3'-succinyl-Icaa CPG-N-acetyl guanine protected nucleosides (group 6). 5'-DMT-2'-TBDMS-N-acetyl protected-guanosine-3'-amidites The invention also contemplates method for preparing the disclosed compositions. The starting base protection with transient protection with TMSChloride/pyridine at low temperature affording N-acetyl protected nucleoside. The products are invariably crystallized.

Following tritylation reaction (with DMT-Chloride) of the nucleoside with DMT chloride in pyridine gave desired nucleoside in high yields for rG, 2'-fluoro-rG, 2'-Omethyl-rguanosine. In the case of 2'-amino, the amino group is protected first with trifluoro methyl group.

Additional Notes for Claims, Structures (i) A method for 3' to 5' direction of oligonucleotide bond formations shown in formula 4 in synthetic RNA oligomers. The RNA could consist of natural of modified nucleo bases as described in claim 1 to synthesize gapmers, phosphodiesters, phosphorothiates, phosphoselenate. One of the nucleoside components will have N-acetyl guanosine base. The synthesis could be performed on automated, semi automated DNA/RNA or other synthesizers or manually. The synthesis can be performed at various scales from microgram to kilogram scales.

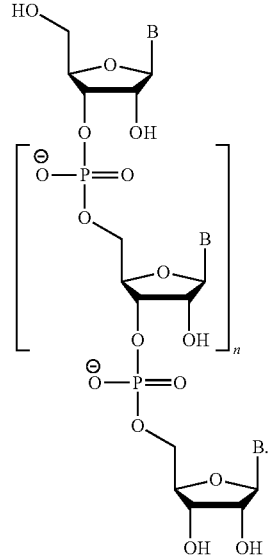

Formula 4

(ii) A method for DNA & RNA synthesis using mild amine, secondary or tertiary amine for removal of N-acetyl protecting group of guanosine and cyanoethyl phosphate protecting group for RNA synthesis via 3' to 5' direction of oligonucleotide bond formations shown in formula 4 in synthetic RNA oligomers. The RNA could consist of natural of modified nucleo bases, gapmers, phosphodiesters, phosphorothiates, phosphoselenate. The nucleoside components will have N-Fmoc as protecting group. The synthesis could be performed on automated, semi automated DNA/RNA or other synthesizers or manually. The synthesis can be performed at various scales from microgram to kilogram scales.

(iii) A method for DNA & RNA synthesis using mild basic conditions, such as methyl amine solution, alkylamines, secondary or tertiary amine for removal of N-acetyl guanosine protecting group and cyanoethyl phosphate protecting group for RNA synthesis via 3' to 5' direction of oligonucleotide bond formations shown in formula 4 in synthetic RNA oligomers. This is followed by wash of liberated protecting groups. The RNA could consist of natural of modified nucleo bases, gapmers, phosphodiesters, phosphorothiates, phosphoselenate. The nucleoside components will have N-Fmoc as protecting group. The synthesis could be performed on automated, semi automated DNA/RNA or other synthesizers or manually. The synthesis can be performed at various scales from microgram to kilogram scales.

(iv) A method for DNA & RNA synthesis using mild basic conditions, such as methyl amine solution, alkylamines, secondary or tertiary amine for removal of N-acetyl guanosine from solid support base as well as nucleosides in the rest of sequence and cyanoethyl phosphate protecting group. DNA and RNA synthesis can be carried out via 3' to 5' direction of oligonucleotide bond formations. This is followed by wash of liberated protecting groups. The support bound DNA and RNA could consist of natural or modified nucleo bases, gapmers, phosphodiesters, phosphorothiates, phosphoselenate. The nucleoside components during such oligo synthesis will have N-acetyl as protecting group. The synthesis could be performed on automated, semi automated DNA/RNA or other synthesizers or manually. The synthesis can be performed at various scales from microgram to kilogram scales.

(v) The modified nucleosides incorporated by this method could consists of one or more of purine or pyrimidine modifications such as but not limited to, 5-Fluoro-U, 5-Fluoro dU, 5-fluoro-dC, 5-Fluro-rC, pseudouridine, 5-methyl-dU, 5-methyl-rU, 5-methyl-dC, 5-methyl-rC, 5-bromo-dU, 5-bromo-rU, 5-bromo-dC, 5-bromo-rC, 5-iodo-dU, 5-iodo-rU, 5-vinyl-dU, 5-vinyl-rU, 5-vinyl thymidine, N-3 methyldeoxy uridine, N-3 methyl-ribouridine, N-3 methyl thymidine, 4-thio uridine, 4-thio-2'-deoxyuridine, 2,6-diaminopurine deoxy riboside, N-3 methyl ribothymidine, 2,6-diaminopurine riboside, 8-bromo 2'-deoxy adenosine, 8-bromo-r-adenosine, 8-oxo-deoxy adenosine, 8-oxo-riboadenosine, 8-oxo-2'-deoxy-adenosine, 8-oxo-riboadenosine, 8-oxo-deoxy inosine, 8-oxo-ribo inosine, 8-bromo-deoxy inosine, 8-bromo-ribo-inosine, N-1 methyl-riboadenosine, N-1 methyl-2'-deoxy adenosine, N-1 methyl 2'-deoxy inosine, N-1 methyl riboadenosine, N-1 methyldeoxy guanosine, N-1-methyl-riboguanosine, etheno adenosine, etheno 2'-deoxy adenosine, purine 2'-deoxy riboside, purine-ribonucleoside, 2-aminopurine-2'-deoxyriboside, 2-aminopurine-ribonucleoside, (vi) Labelling of internal positions of an RNA synthesized by this methods with chromophores such as, but not limited to Fluoroscein-C-5 dT, Dabcyl-C-5 thymidine, internal carboxyl group 5-dU-methylacrylate, biotin dT (biotin wattached via spacer to C-5 of dU), amino-dT (terminal amino attached via C-6 spacer to C-5 dU).

(vii) The sugar modification of modified nucleosides could consist of 2'-deoxy-2'-fluoro ribo nucleosides (2'-F-ANAs) such as A, C, G, U, Inosine and modified nucleosides containing 2'-Fluoro, in one or more positions of an RNA or DNA sequence synthesized by this method.

(viii) The sugar modification of modified nucleosides could consist of 2'-deoxy-2'-methoxy ribo nucleosides (2'-OMe-) such as A, C, G, U, Inosine and modified nucleosides containing 2'-methoxy, in one or more positions of an RNA or DNA sequence synthesized by this method.

(ix) The sugar modification of modified nucleosides could consist of 2'-deoxy-2'-amino ribo nucleosides (2'-NH2) such as A, C, G, U, Inosine and modified nucleosides containing 2'-amino, in one or more positions of an RNA or DNA sequence synthesized by this method.

(x) The sugar modification of modified nucleosides could consist of 2'-deoxy-2'-terminal amino ribo nucleosides (2'-terminal NH2), attached via spacer from 2-10 atoms on nucleosides such as A, C, G, U, Inosine and modified nucleosides containing 2'-terminal amino, in one or more positions of an RNA or DNA sequence synthesized by this method.

(xi) The sugar modification of modified nucleosides could consist of 2'-deoxy-2'-methoxy ethoxy ribo nucleosides (2'-MOE), such as A, C, G, U, Inosine and modified nucleosides containing 2'-MOE, in one or more positions of an RNA or DNA sequence synthesized by this method.

(xii) The sugar modification of modified nucleosides could consist of other 2'-O-alkyl groups, such as 2'-deoxy-2'-ethoxy, propargyl, butyne ribo nucleosides (2'-OEt, O-Propargyl, 2'-O-Butyne), such as A, C, G, U, Inosine and modified nucleosides containing 2'-2'-OEt, O-Propargyl, 2'-O-Butyne, in one or more positions of an RNA or DNA sequence synthesized by this method.

(xiii) The sugar modification of modified nucleosides could consist of 2'-deoxy-2'-fluoro arabino nucleosides (2'-F-ANAs) such as A, C, G, U, Inosine and modified nucleosides containing 2'-F-ANAs), in one or more positions of an RNA or DNA sequence synthesized by this method.

(xiv) The sugar modification of modified nucleosides could consist of 2'-deoxy-2'-fluoro 4'-thioarabino nucleosides (4'-S-FANAs) such as A, C, G, U, Inosine and modified nucleosides containing 4'-S-FANAs in one or more positions of an RNA or DNA sequence synthesized by this method.

(xv) The RNA comprising one or more 2'-5'-linkage within the sequence, at the 3'-end of the sequence or at the 5'-end of the sequence.

(xvi) The RNA having a 3'-end, synthesized by the method of this invention containing reverse attached deoxy nucleosides such as dT, dC, dG, thymidine, attached via their 3'-hydroxyl function.

(xvii) The RNA having a 3'-end synthesized by the method of this invention containing reverse attached ribonucleosides such as rA, rC, rG, rU, attached via their 2' or 3'-hydroxyl function.

(xviii) The RNA synthesis comprising 2'-triisopropylsilyloxy methyl (TOM), protecting group.

(xix) The RNA synthesis comprising 2'-t-butyldithiomethyl (DTM) protecting group.

(xx) The reverse RNA synthesis comprising the modified base comprising 2'-deoxy-2'-fluoro-beta-D_arabino-nucleic acid (FANA).

(xxi) The RNA synthesis comprising the modified base comprising 4'-thio-2'-deoxy-2'-fluoro-beta-D_arabino-nucleic acid (4'-Thio-FANA).

(xxii) The RNA synthesis comprising the modified sugar comprising 2'-OMethyl modification.

(xxiii) The RNA synthesis comprising the modified sugar comprising Bicyclic locked nucleic acids (LNA's).

(xxiv) The RNA synthesis comprising the modified sugar altritol sugar to lead to modified oligonucleotides (ANA).

(xxv) The RNA synthesis comprising the step of conjugation of peptides, such as cell penetrating peptides (CPPs) or membrane permeant peptide (MPPs) utilizing either the free amine function of such peptides and a 3'-terminal carboxylic function on the reverse synthesized RNA. The CPPs and MPPs having an appropriate carboxyl function can be coupled to the free terminal amino function of an FMOC protected nucleotide or an oligonuleotide.

(xxvi) The DNA and RNA synthesis comprising the 2'-5'-linked DNA units or 2'-5'-RNA units within the sequence, at the 3'-end of the sequence or at the 5'-end of the sequence.

Based on the foregoing disclosure and experimental results obtained which have been reported in the drawing figures herein, and in the earlier patent applications of ChemGenes Corporation,

We claim:

1. Derivatized nucleoside and phosphoramidite of general formula 1,

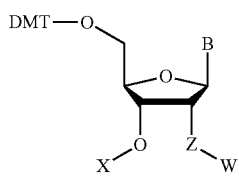

Formula 1 where B is selected from the group consisting of Guanine-N-acetyl, adenine-N-acetyl, cytosine-N-acetyl, cytosine-N-isobutyryl, 5-methyl cytosine-N-acetyl, and 5-methyl cytosine-N-isobutyryl;

Z is Oxygen and W is methyl; and

X is cyanoethyl dialkyl phosphoramidite.

2. Derivatized nucleoside and phosphoramidite of general formula 1,

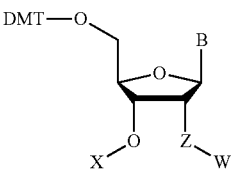

(Formula 1)

where B is Guanine-N-acetyl, or adenine-N-acetyl;

Z=ribo Fluoro or ara fluoro, and

W is absent; and

X is cyanoethyl dialkyl phosphoramidite.

3. Derivatized nucleosides, succinates and solid supports of general formula 2,

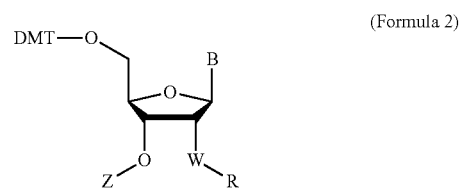

(Formula 2)

where B is Guanine-N-acetyl, or adenine-N-acetyl;

W=ribo fluoro or ara fluoro, and R is absent;

Z is C(O)-M-C(O)—NH, where M is selected from the group consisting of succinyl, oxalyl, and hydroquinolynyl, and NH is capable of being attached to a solid support with a spacer selected from the group consisting of C1-C20 alkyl, ethyloxyglycol, and a combination of alkyl and ethyleneglycoxy.

4. Derivatized nucleosides, succinates and solid supports of general formula 2,

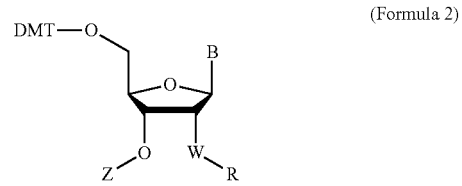

(Formula 2)

wherein, B is selected from the group consisting of Guanine-N-acetyl, adenine-N-acetyl, cytosine-N-acetyl, cytosine-N-isobutyryl, 5-methyl cytosine-N-acetyl, and 5-methyl cytosine-N-isobutyryl;

W is Oxygen and R is selected from the group consisting of t-Butyldimethyl silyl, acetal levulinyl ester (ALE), pivaloyloxy, cyanoethylmethylene (CEM), dithiomethylene (DTM)); and Z is C(O)-M-C(O)—NH, where M is selected from the group consisting of succinyl, oxalyl, and hydroquinolynyl, and NH is capable of being attached to a solid support with a spacer selected from the group consisting of C1-C20 alkyl, ethyloxyglycol, and a combination of alkyl and ethyleneglycoxy.

5. Derivatized nucleosides, succinates and supports of general formula 2,

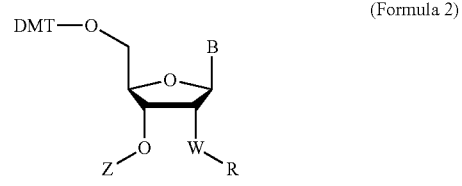

(Formula 2)

wherein B is selected from the group consisting of Guanine-N-acetyl, adenine-N-acetyl, cytosine-N-acetyl, cytosine-N-isobutyryl, 5-methyl cytosine-N-acetyl, and 5-methyl cytosine-N-isobutyryl;

W is Oxygen and R is methyl; and

Z is C(O)-M-C(O)—NH, where M is selected from the group consisting of succinyl, oxalyl, and hydroquinolynyl, and NH is C1-C20 alkyl, ethyloxyglycol, and a combination of alkyl and ethyleneglycoxy.

* * * * *

(12) INTER PARTES REVIEW CERTIFICATE (3791st)

United States Patent
Srivastava et al.

(10) Number: US 9,884,885 K1
(45) Certificate Issued: Oct. 28, 2024

(54) SYNTHESIS OF LABILE BASE PROTECTED—MODIFIED DEOXY AND MODIFIED RIBO NUCLEOSIDES, CORRESPONDING PHOSPHORAMIDITES AND SUPPORTS AND THEIR USE IN HIGH PURITY OLIGONUCLEOTIDE SYNTHESIS

(75) Inventors: Suresh C. Srivastava; Naveen P. Srivastava

(73) Assignee: CHEMGENES CORPORATION

Trial Number:

IPR2023-00490 filed Jan. 19, 2023

Inter Partes Review Certificate for:

Patent No.: 9,884,885
Issued: Feb. 6, 2018
Appl. No.: 13/261,029
Filed: Nov. 18, 2011

The results of IPR2023-00490 are reflected in this inter partes review certificate under 35 U.S.C. 318(b).

INTER PARTES REVIEW CERTIFICATE
U.S. Patent 9,884,885 K1
Trial No. IPR2023-00490
Certificate Issued Oct. 28, 2024

AS A RESULT OF THE INTER PARTES REVIEW PROCEEDING, IT HAS BEEN DETERMINED THAT:

Claims 1-5 are cancelled.

\* \* \* \* \*